(12) United States Patent
Smith et al.

(10) Patent No.: US 8,124,794 B2
(45) Date of Patent: Feb. 28, 2012

(54) METHOD FOR THE ASYMMETRIC SYNTHESIS OF BETA-LACTONE COMPOUNDS

(75) Inventors: Jeffrey W. Smith, La Jolla, CA (US); Fumiko Axelrod, La Jolla, CA (US); Steven J. Kridel, La Jolla, CA (US); Daniel Romo, College Station, TX (US); Vikram Purohit, College Station, TX (US); Gil Ma, College Station, TX (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 12/620,412

(22) Filed: Nov. 17, 2009

(65) Prior Publication Data

US 2010/0173982 A1 Jul. 8, 2010

Related U.S. Application Data

(62) Division of application No. 11/378,961, filed on Mar. 16, 2006, now Pat. No. 7,728,153.

(51) Int. Cl.
*C07D 305/00* (2006.01)

(52) U.S. Cl. ......... 549/263; 549/327; 549/328; 549/329

(58) Field of Classification Search .................. 549/263, 549/327, 328, 329
See application file for complete search history.

(56) References Cited

U.S. PATENT DOCUMENTS

| | | | |
|---|---|---|---|
| 4,598,089 A | 7/1986 | Hadvary | |
| 4,806,564 A | 2/1989 | Chabala | |
| 4,873,260 A | 10/1989 | Alberts | |
| 4,931,463 A | 6/1990 | Barbier | |
| 4,983,746 A | 1/1991 | Barbier | |
| 5,175,186 A | 12/1992 | Barbier | |
| 5,246,960 A | 9/1993 | Barbier | |
| 5,260,310 A | 11/1993 | Derungs | |
| 5,376,674 A | 12/1994 | Derungs | |
| 5,399,720 A | 3/1995 | Karpf | |
| 5,466,708 A | 11/1995 | Derungs | |
| 5,759,837 A | 6/1998 | Kuhajda | |
| 5,981,771 A | 11/1999 | Okeda | |
| 7,728,153 B2 * | 6/2010 | Smith et al. ................... | 549/263 |
| 7,799,826 B2 | 9/2010 | Smith | |
| 2008/0124681 A1 | 5/2008 | Cha | |
| 2010/0173982 A1 | 7/2010 | Smith | |

FOREIGN PATENT DOCUMENTS

| | | |
|---|---|---|
| EP | 0185359 | 12/1985 |
| JP | 3115274 | 5/1991 |
| WO | 0004300 | 1/2000 |
| WO | 0224674 | 3/2002 |

OTHER PUBLICATIONS

Yang et al. Tetrahedron (1997), 53(48), 16471-16488.*
Mageswaran et al. Journal of the Chemical Society, Perkin Transactions 1: Organic and Bio-Organic Chemistry (1972-1999) (1976), (8), 884-90.*
Umezawa et al. Journal of Antibiotics (1978), 31(8), 797-800.*
Mulzer et al. Journal of the American Chemical Society (1980),102(10), 3620-2.*
Alo, et al., "Expression of fatty acid synthase (FAS) as a predictor of recurrence in stage I breast carcinoma patients", Cancer, 77:474-82 (1996).
Auerbach and Auerbach, "Angiogenesis inhibition: a review", Pharmac. Ther., 63:265-311 (1994).
Calter, "Catalytic, Asymmetric Dimerization of Methylketene", J. Organic Chemistry, 61:8006 (1996).
Creamer and Barker, "Vascular proliferation and angiogenic factors in psoriasis", Clin. Exp. Dermatol., 20:6-9 (1995).
DeVos, et al., "Cellular pharmacology of cerulenin analogs that inhibit protein palmitoylation", Biochem. Pharmcol., 62:985-995 (2001).
Folkman, "Angiogenesis in cancer, vascular, rheumatoid and other disease", Nat. Med., 1(1):27-31 (1995).
Greenbaum, et al., "Epoxide electrophiles as activity-dependent cysteine protease profiling and discovery tools", Chem. Biol., 7:569-581 (2000).
Hadvary, et al., "The lipase inhibitor tetrahydrolipstatin binds covalently to the putative active site serine of pancreatic lipase", J. Biol. Chem., 266(4):2021-27 (1991).
Harvey, et al., "Insights into a plasma membrane signature", Physiol. Genomics., 5:129-36 (2001).
Jochen, et al., "Inhibitory effects of cerulenin on protein palmitoylation and insulin internalization in rat adipocytes", Biochim. Biophys. Acta., 1259:65-72 (1995).
Johnson, et al, "Relationships between drug activity in NCI preclinical in vitro and in vivo models and early clinical trials", British J of Cancer, 84(10):1424-31 (2001).
Kidd, et al., "Profiling serine hydrolase activities in complex proteomes", Biochemistry, 40:4005-15 (2001).
Kridel, et al., "Orlistat is a novel inhibitor of fatty acid synthase with antitumor activity", Cancer Res., 64:2070-75 (2004).
Kuhajda, "Fatty-acid synthase and human cancer: new perspectives on its role in tumor biology", Nutrition, 16:202-208 (2000).
Kuhajda, et al., "Fatty acid synthesis: a potential selective target for antineoplastic therapy", PNAS, 91:6379-83 (1994).
Kuhajda, et al., "Synthesis and antitumor activity of an inhibitor of fatty acid synthase", PNAS, 97:3450-54 (2000).

(Continued)

*Primary Examiner* — Nizal Chandrakumar
(74) *Attorney, Agent, or Firm* — Pabst Patent Group LLP

(57) ABSTRACT

The present invention features methods of treating a cancer in a subject by administering an effective amount of a beta-lactone to the subject. The invention also features methods of inhibiting angiogenesis in a subject by administering an effective amount of an inhibitor of fatty acid synthase to the subject. These methods can be used to treat a variety of cancers and other diseases and conditions. The invention also features methods of identifying beta-lactones and other compounds that can be used in the methods of the invention for the treatment of tumors, inhibition of angiogenesis, and the treatment of diseases and conditions that involve pathological angiogenesis. The invention also features methods of synthesizing beta-lactones and features novel beta-lactone compounds.

30 Claims, 9 Drawing Sheets

OTHER PUBLICATIONS

Kurebayashi, et al., "Quantitative demonstration of spontaneous metastasis by MCF-7 human breast cancer cells cotransfected with fibroblast growth factor 4 and LacZ", Cancer Res., 53:2178-87 (1993).

Landry, et al., "A method for application of samples to matrix-assisted laser desorption ionization time-of-flight targets that enhances peptide detection", Anal. Biochem., 279:1-8 (2000).

Lawrence, et al, "Structure-activity studies of cerulenin analogues as protein palmitoylation inhibitors", J Med. Chem., 42:4932-41 (1999).

Li, et al., "Pharmacological inhibition of fatty acid synthase activity produces both cytostatic and cytotoxic effects modulated by p53", Cancer Res., 61:1493-99 (2001).

Liu, et al., "Activity-based protein profiling: the serine hydrolases", PNAS, 96 (26):14694-99 (1999).

McNeely and Benfield, "Orlistat", Drugs, 56(2):241-49 (1998).

Paterson and Hulme, "Total Synthesis of (-)-Ebelactone A and B", J Org. Chem., 60(11):3288-3300 (1995).

Patricelli, et al., "Direct visulization of serine hydrolase activities in complex proteomes using fluorescent active site-directed probes", Proteomics, 1:1067-71 (2001).

Pizer, et al., "Fatty acid synthase (FAS): a target for cytotoxic antimetabolites in HL60 promyelocytic leukemia cells", Cancer Res., 56:745-51 (1996).

Pizer, et al., "Increased fatty acid synthase as a therapeutic target in androgen-independent prostate cancer progression", Prostate, 47:102-110 (2001).

Pizer, et al., "Malonyl-coenzyme-A is a potential mediator of cytotoxicity induced by fatty-acid synthase inhibition in human breast cancer cells and xenografts", Cancer Res., 60:213-218 (2000).

Pizer, et al., "Pharmacological inhibitors of mammalian fatty acid synthase suppress DNA replication and induce apoptosis in tumor cell lines", Cancer Res., 58:4611-4615 (1998).

Price, et al., "Tumorigenicity and metastasis of human breast carcinoma cell lines in nude mice", Cancer Res., 50:717-721 (1990).

Purohit, et al., "Practical, catalytic, asymmetric synthesis of beta-lactones via a sequential ketene dimerization/hydrogenation process: inhibitors of the thioesterase domain of fatty acid synthase", J Organic Chemistry, 71:4549-58 (2006).

Robbins, Pharmacisits in the Industry, Remington: The Science and Practice of Pharmacy (19th ed) ed:29-31 (1995).

Richardson, et al., "Synthesis of Novel $^2$-Lactone Inhibitors of fatty acid synthase", J. Med. Chem., 51:5285-96 (2008).

Salcedo, et al., "Human endothelial cells express CCR2 and respond to MCP-1: direct role of MCP-1 in angiogenesis and tumor progression", Blood, 96:34-40 (2000).

Sauer, "Ketene Dimers from Acid Halides", J of Am. Chemical Society, 69 (10):2444-48 (1947).

Sausville, et al., "Contributions of human tumor xenografts to anti-cancer drug development", Cancer Research, 66:3351-54 (2006).

Shafie, et al., "Formation of metastasis by human breast carcinoma cells (MCF-7) in nude mice", Cancer Lett., 11:81-87 (1980).

Thupari, et al., "Fatty acid synthase inhibition in human breast cancer cells leads to malonyl-CoA-induced inhibition of fatty acid oxidation and cytotoxicity", Biochem. Biophys. Res. Commun., 285(2):217-223 (2001).

Tomoda, et al., "Synthesis of Four Chiral Isomers of beta-Lactone DU-6622 and Inhibition of HMG-CoA Synthase by the Specific (2R,3R)-Isomer", J Organic Chemistry, 62:2161-65 (1997).

Umezawa, et al., "Ebelactone, an inhibitor of esterase, produced by actinomycetes", J Antibiot. (Tokyo), 33(12):1594-96 (1980).

Uotani, et al., "Structural studies on ebelactone A and B, esterase inhibitors produced by actinomycetes", J. Antibiot. (Tokyo), 35(11):1495-99 (1982).

\* cited by examiner

US 8,124,794 B2

METHOD FOR THE ASYMMETRIC SYNTHESIS OF BETA-LACTONE COMPOUNDS

PRIORITY APPLICATION INFORMATION

This application is a divisional of and claims priority to U.S. application Ser. No. 11/378,961, filed on Mar. 16, 2006 now U.S. Pat. No. 7,728,153, and which claims priority to U.S. application Ser. No. 10/418,513, pending, filed Apr. 16, 2003, and which are hereby incorporated by reference in their entirety.

STATEMENT OF FEDERALLY SPONSORED RESEARCH

This invention was made with government support under Grant No. CA 69036 awarded by the National Institutes of Health. The government has certain rights in the invention.

FIELD OF THE INVENTION

This invention relates generally to beta-lactones to inhibit the enzymatic activity of fatty acid synthase.

BACKGROUND OF THE INVENTION

Fatty acid synthase (FAS) is a multifunctional enzyme that catalyzes the synthesis of long-chain fatty acids from small carbon substrates. The enzyme contains six separate enzymatic pockets along with an acyl carrier protein, which act sequentially to perform repeated condensations of acetyl CoA and malonyl CoA, yielding predominantly palmitate, a sixteen-carbon polyunsaturated fatty acid. Following seven such condensation cycles, palmitate remains covalently attached to the acyl carrier protein of the enzyme until it is liberated by the final enzymatic pocket on the enzyme, the intrinsic thioesterase.

Fatty acid synthesis has long been thought unimportant in most normal tissues, and the enzyme is down-regulated by dietary lipid. However, increased FAS expression and activity in tumors is well documented. Tumor cell dependence on de novo fatty acid synthesis is viewed as a metabolic anomaly, with the endogenously-synthesized fatty acids apparently incorporated into membrane phospholipids in preparation for cell division.

Given the prevalence of cancer that is refractory to current therapies, there is a need for new cancer treatment strategies.

Moreover, there is a need for new compounds useful for providing cancer therapy treatments.

SUMMARY OF THE INVENTION

Described herein are asymmetric beta-lactones compounds and methods for their synthesis.

The invention includes methods for the asymmetric synthesis of beta-lactone compounds comprising the steps of forming a ketene dimer from an acid chloride; and hydrogenating the ketene dimer to generate a cis-beta-lactone.

In some embodiments the method is a one-pot synthesis method. In some embodiments the ketene dimer formed is isolated before the hydrogenation step.

In some embodiments of the method the isolation of the ketene dimer is by silica gel purification.

In some embodiments of the method the acid chloride has the formula VII wherein R comprises a hydrogen, an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group or a sulfo-oxo group.

In some embodiments of the method the R comprises n-butyl, cyclopentyl, cyclohexyl, benzyl, $CH_2CO_2Me$ or 11-methoxynonyl or n-butyl.

In some embodiments of the method the step of forming a ketene dimer from an acid chloride comprises using a catalyst wherein said catalyst is selected from the group consisting of QND, O-TBS QND, O-TMS QND, and O-TMS QUIN.

In some embodiments of the method the step of hydrogenating the ketene dimer comprises using a palladium on carbon catalyst, which can be at a concentration of about between 1 mol % and 5 mol %.

In some embodiments of the method the catalyst is accompanied by an amine which can be triethylamine.

In some embodiments of the method the step of hydrogenating a ketene dimer is performed for 30 minutes at 30 psi $H_2$.

In some embodiments the method can further include an epimerization step.

In some embodiments of the method the epimerization step comprises the further steps of deprotonating the cis-beta lactone; and quenching the deprotonated species under low temperature.

In some embodiments of the method the step of deprotonating is performed using lithium hexamethyldisilazide (LiHMDS), or related bases such as lithium diisopropylamide (LDA), sodium hexamethyldisilazide (NaHMDS), or lithium tetramethylpiperidide (LiTMP).

In some embodiments of the method the step of quenching the deprotonated species is performed using acetic acid.

In some embodiments the method may further include converting the cis-beta-lactone to a trisubstituted species. In some embodiments of the method the converting step includes alkylation or acylation.

In some embodiments the method further includes enolization of the cis-beta-lactone; and addition of electrophiles.

In some embodiments of the method the enolization step is performed using LDA, LiHMDS or NaHMDS.

In some embodiments of the method the electrophiles added to the enolated species are selected from the group consisting of electrophiles.

In some embodiments of the method the electrophile is a bulky electrophile or a smaller electrophile. In some embodiments the method the electrophile comprises $CH_3$, Benzyl or $CO_2Me$.

In some embodiments the invention is a compound synthesized by the inventive methods.

In some embodiments the invention is a compound of formula VI wherein $R^1$, $R^2$, $R^3$, and $R^4$ independently comprise a hydrogen, an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group, or a combination thereof, and wherein the stereochemistry at carbons a and b is R or S.

In some embodiments the invention is a compound of formula wherein R comprises n-butyl, cyclopentyl, cyclohexyl, benzyl, $CH_2CO_2Me$ or 11-methoxynonyl. In some embodiments the invention is a compound of formula VI wherein R1 and R4 are n-butyl and R2 and R3 are hydrogen.

In some embodiments the invention is a compound of formula VI wherein the compound is a compound selected from the group consisting of (3R,4S)-3-butyl-4-pentyloxetan-2-one, (3R,4R)-3-butyl-4-pentyloxetan-2-one; (3R,4S)-3-butyl-3-methyl-4-pentyloxetan-2-one; (3S,4S)-3-benzyl-3-butyl-4-pentyloxetan-2-one; and (3S,4S)-benzyl 3-butyl-2-oxo-4-pentyloxetane-3-carboxylate.

In some embodiments the invention is a compound of formula VI wherein the compound is synthesized using a method comprising the steps of forming a ketene dimer from an acid chloride; and hydrogenating the ketene dimer to generate a cis-beta-lactone.

In some embodiments the invention is a compound of claim formula VI wherein said compound is synthesized using a method comprising the steps of forming a ketene dimer from an acid chloride; hydrogenating the ketene dimer to generate a cis-beta-lactone; and epimerization step further comprising the steps of deprotonating the cis-beta lactone; and quenching the deprotonated species under low temperature.

In some embodiments the invention is a compound of claim formula wherein the compound is synthesized using a method comprising the steps of forming a ketene dimer from an acid chloride; hydrogenating the ketene dimer to generate a cis-beta-lactone; and converting the cis-beta-lactone to a trisubstituted species.

In some embodiments the invention is a method of inhibiting a serine hydrolase comprising administering an effective amount of a beta-lactone.

In some embodiments of the methods the serine hydrolase is selected form the group consisting of lipase, protease and esterase.

In some embodiments of the methods the serine hydrolase is fatty acid synthase.

In some embodiments of the methods the beta-lactone comprises a formula I compound wherein $R^1$, $R^2$, $R^3$, and $R^4$ are, independently, hydrogen, an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group, or a combination thereof, and wherein the stereochemistry at carbons a and b is R or S.

In some embodiments of the methods the beta-lactone comprises a formula VI compound wherein $R^1$, $R^2$, $R^3$, and $R^4$ independently comprise a hydrogen, an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group, or a combination thereof, and wherein the stereochemistry at carbons a and b is R or S.

In any of the above aspects of the invention, the beta-lactone can be any beta-lactone (or any combination of beta-lactones), for example, but not limited to, a beta-lactone wherein $R^1$ is a straight-chain alkyl group (e.g., but not limited to, tetrahydrolipstatin, ebelactone A, or ebelactone B).

In any of the above aspects of the invention, the beta lactone can have the formula I:

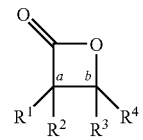

wherein $R^1$, $R^2$, $R^3$, and $R^4$ are, independently, hydrogen, an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group, or a combination thereof, and wherein the stereochemistry at carbons a and b is R or S, as described herein.

Alternatively in the invention, the beta lactone can have the formula VI:

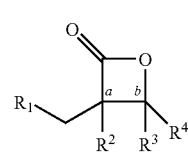

wherein $R^1$, $R^2$, $R^3$, and $R^4$ are, independently, hydrogen, an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group, or a combination thereof, and wherein the stereochemistry at carbons a and b is R or S, as described herein.

For example, in various embodiments of any of the above aspects of the invention, $R^2$ and $R^4$ are hydrogen. Moreover, in various embodiments of any of the above aspects of the invention, $R^1$ is an alkyl group, for example, a straight chain $C_1$ to $C_{20}$ alkyl group. In still other embodiments, $R^3$ is an alkyl group comprising an ester group (for example, a straight chain $C_3$ to $C_{20}$ alkyl group); moreover, the ester group can further comprise an amide group. In yet other embodiments, $R^3$ is an alkenyl group (for example, a straight chain $C_3$ to $C_{20}$ alkenyl group) comprising an ester group; moreover, the ester group can further comprise an amide group.

In still other embodiments of any of the above aspects of the invention, $R^2$ and $R^4$ are hydrogen, the stereochemistry at carbon a is S, and the stereochemistry at carbon b is S; moreover, $R^1$ can be an alkyl group or an alkenyl group. For example, in some embodiments of any of the above aspects of the invention, $R^1$ is an alkyl group, $R^2$ and $R^4$ are hydrogen, $R^3$ is an alkyl group comprising an ester group, the stereochemistry at carbon a is S, and the stereochemistry at carbon b is S. In other embodiments of any of the above aspects of the invention, $R^1$ is an alkyl group, $R^2$ and $R^4$ are hydrogen, $R^3$ is an alkenyl group comprising an ester group, the stereochemistry at carbon a is S, and the stereochemistry at carbon b is S. For example, the compound can be tetrahydrolipstatin or lipstatin.

In yet other embodiments of any of the above aspects of the invention, $R^2$ and $R^4$ are hydrogen, and $R^1$ is a $C_1$ to $C_5$ alkyl group. For example, the alkyl group can be methyl, ethyl, propyl, isopropyl, butyl, isobutyl, or tert-butyl.

In yet other embodiments of any of the above aspects of the invention, $R^3$ is a $C_3$ to $C_{20}$ alkenyl group comprising at least one hydroxyl group or at least one protected hydroxyl group. Moreover, the alkenyl group can further comprise a carbonyl group. For example, in some embodiments of any of the above aspects of the invention, $R^1$ is an alkyl group (for example, a methyl or ethyl group), $R^2$ and $R^4$ are hydrogen, $R^3$ is an alkenyl group comprising at least one hydroxyl group or at least one protected hydroxyl group, the stereochemistry at carbon a is S, and the stereochemistry at carbon b is S.

In various embodiments of any of the above aspects of the invention, the compound can be ebelactone A or ebelactone B.

Additional advantages of the invention will be set forth in part in the description which follows, and in part will be apparent from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

Figure 1:
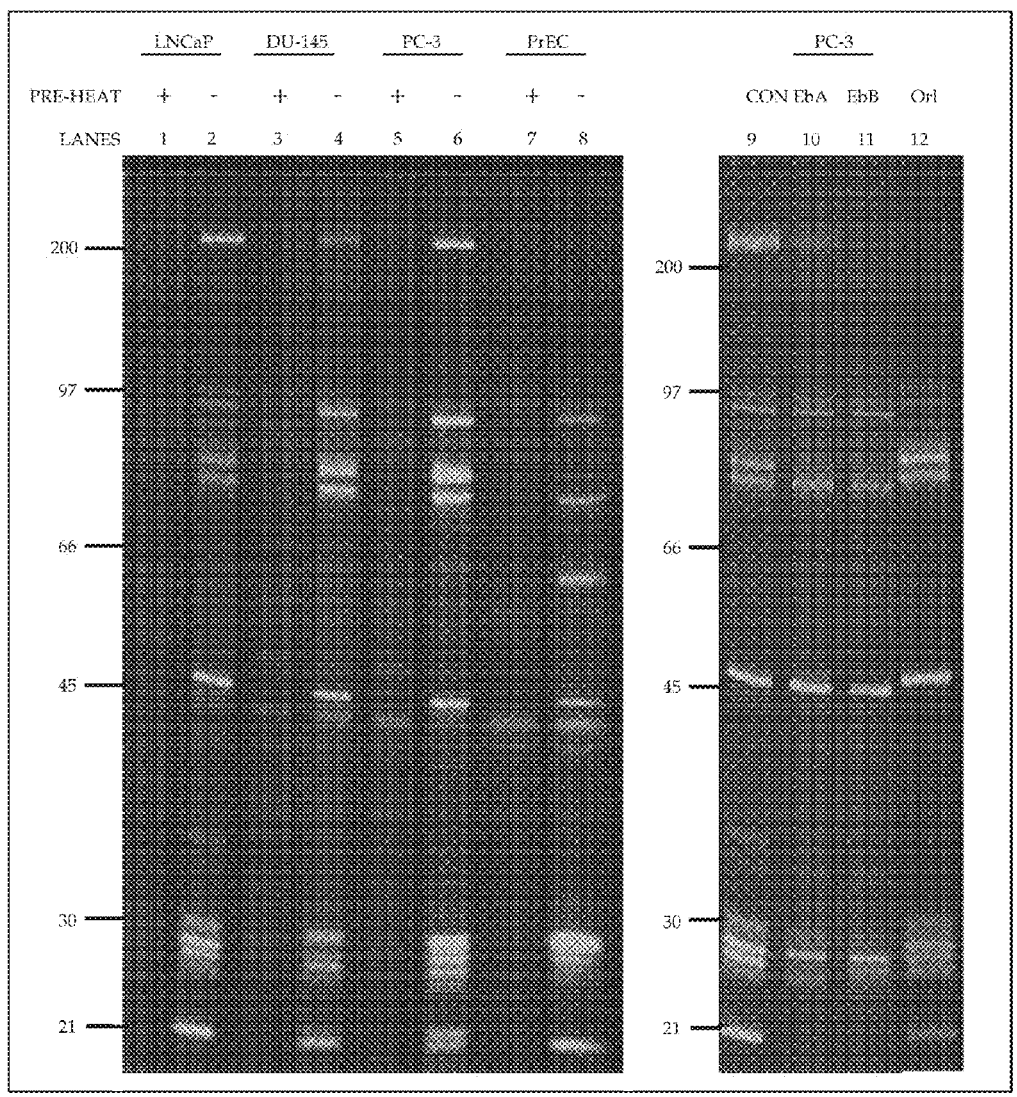
FIG. 1 shows a scan of an SDS-polyacrylamide gel that displays the serine hydrolase activity profile for normal and neoplastic prostate epithelial cells.

The present invention is based on the surprising discovery that beta-lactone compounds can be used to inhibit serine hydrolase enzyme activity. Fatty acid synthase (FAS), an enzyme known to be up-regulated in tumor cells, and which has been linked to tumor cell proliferation. As shown herein, treatment of tumor cells with beta-lactone compounds induces cell cycle arrest and/or apoptosis, thereby preventing tumor cell proliferation and/or survival.

Described herein are activity-based profiling studies of serine hydrolases, a large gene family encompassing lipases, proteases, and esterases. The objective was to identify serine hydrolases that represent unique points for therapeutic intervention in cancer, using an activity-based profiling assay to screen for small molecule antagonists. In this screening method, the active site of the serine hydrolases is covalently tagged with a probe comprised of fluorophosphonate linked to a reporter (Liu et al. "Activity-based protein profiling: the serine hydrolases." *Proc. Natl. Acad. Sci. U.S.A* 96:14694-9, 1999).

A fluorescently-tagged fluorophosphonate probe (FP-TAMRA) was used to define the profile of serine hydrolases in carcinoma cells, and to identify inhibitors of these enzymes from a small set of beta-lactones. Specifically, three beta-lactones were tested for the ability to block labeling, by FP-TAMRA, of serine hydrolases expressed by mammary carcinoma and prostate carcinoma cells. These beta-lactones included ebelactones A and B, related natural products from actinomycetes (Umezawa et al. "Ebelactone, an inhibitor of esterase, produced by actinomycetes." *J. Antibiot. (Tokyo).* 33:1594-1596, 1980; and Uotani et al. "Structural studies on ebelactone A and B, esterase inhibitors produced by actinomycetes." *J. Antibiot. (Tokyo).* 35:1495-1499, 1982). Another beta-lactone that was tested was tetrahydrolipstatin, a compound also known as orlistat. Orlistat is a synthetic derivative of the natural product lipstatin, produced by *streptomyces*. Like a majority of the naturally-occurring beta-lactones, orlistat possesses trans-beta lactone stereochemistry. Orlistat is a drug that has been approved by the Food and Drug Administration (FDA) for weight management in obese patients (McNeely and Benfield. "Orlistat." *Drugs* 56:241-9; discussion 250, 1998). Its effectiveness is attributed to its ability to prevent absorption of dietary fat by virtue of its inhibition of pancreatic lipase in the gastrointestinal tract.

All beta-lactones tested inhibited the enzymatic activity of fatty acid synthase (FAS), one of the prominent serine hydrolases identified in our assay. Additional experiments revealed that, surprisingly, orlistat elicits cell cycle arrest in tumor cells at the $G_1/S$ boundary, and, in more differentiated tumor cells, apoptosis soon follows. These discoveries reveal a surprising and unappreciated anti-tumor activity for orlistat and other beta-lactone compounds. Accordingly, any beta-lactone, such as (but not limited to) those described herein, can be used in the methods of the invention to treat or prevent tumors that express FAS. Such treatment inhibits tumor cell proliferation and/or induces tumor cell death. Similarly, the methods of the invention can be used to treat or prevent any tumor that overexpresses FAS (e.g., tumors containing cells that express higher levels of FAS than their normal counterparts, e.g., levels that are at least: 10%, 25%, 50%, 75%, 90%, 2-fold, 3-fold, 5-fold or 10-fold higher than their non-tumor cell counterparts).

In its FDA-approved formulation, orlistat is administered orally, and the effects of the drug are largely confined to the gastrointestinal tract, where it inactivates pancreatic lipase. We have found that orlistat blocks fatty acid synthase activity and induces apoptosis in a number of colon cancer cell lines. Accordingly, orlistat can be administered to patients identified as being in need of therapy for the treatment of colon cancer. In addition, orlistat can be administered prophylactically to patients who are identified as being at relatively high risk for developing colon cancer (e.g., a patient who is in remission from colon cancer, a patient whose family has a higher than normal rate of colon cancer, a patient who has one or more genetic mutations that increase the risk of developing colon cancer (e.g., a mutation in the p53 gene), and/or a patient who has or who has had a disease or condition that increases the risk of developing colon cancer); such patients are readily identified by those of skill in the art.

For other tumors (for example, but not limited to, those of the mammary and prostate gland), orlistat can be administered via a different route (e.g., intravenously), or in a different formulation. Those of ordinary skill in the art will readily be able to identify patients who should receive treatment according to the methods of the invention for a cancer, or patients who should receive prophylactic treatment on account of having a higher than normal risk of developing a cancer that can be treated according to the methods of the invention. For example, a patient who is in remission from cancer, a patient whose family has a higher than normal rate of cancer, a patient who has one or more genetic mutations that increase the risk of developing a cancer (e.g., BRCA-1 mutations indicate a higher than normal risk of breast cancer), a patient who has had a laboratory test or medical diagnostic procedure that indicates a higher than normal risk of cancer (e.g., a high level of prostate-specific antigen (PSA) indicates a higher than normal risk for prostate cancer, and the presence of colon polyps, as revealed by colonoscopy, indicates a risk for colon cancer), and/or a patient who has or who has had a disease or condition that increases the risk of developing a cancer (e.g., women who have had breast cancer are in some cases considered by those of skill in the art to have a higher risk of developing endometrial cancer), can be considered as candidates for prophylactic treatment to decrease the likelihood of developing a cancer that could be treated according to the methods of the invention.

The present invention also provides methods based upon a second surprising discovery, i.e., the discovery that FAS is expressed by endothelial cells (the cells that form blood vessels), and is necessary for the proliferation of endothelial cells and for angiogenesis. Angiogenesis, also known as neovascularization, is the process by which endothelial cells infiltrate a tissue, remodel to form blood vessels, and ultimately deliver blood to the tissue. A wide range of physiologic and pathophysiologic processes require angiogenesis, including development, adipogenesis, psoriasis, macular degeneration, and tumor growth and metastasis (see, e.g., Auerbach, W. and Auerbach, R. "Angiogenesis inhibition: a review." *Pharmacol. Ther.* 63:265-311, 1994; Folkman, J. "Angiogenesis in cancer, vascular, rheumatoid and other disease." *Nat. Med.* 1:27-31, 1995; and Creamer, J. D. and Barker, J. N. "Vascular proliferation and angiogenic factors in psoriasis." *Clin. Exp. Dermatol.* 20:6-9, 1995).

The experiments described herein show that FAS is necessary for the proliferation of endothelial cells and for angiogenesis, and that inhibition of FAS activity in endothelial cells inhibits mitogenesis and induces cell cycle arrest. Accordingly, the present invention provides methods for inhibiting angiogenesis and for treating and/or preventing cancers and other diseases that involve pathological angiogenesis, by administering compounds that inhibit FAS activity, thereby inhibiting angiogenesis and treating and/or preventing the disease.

Inhibitors or antagonists of FAS activity can be used in the methods of the invention as anti-angiogenic factors to treat and/or prevent any disease or condition that involves pathological angiogenesis (i.e., angiogenesis that allows a disease or condition to initially develop, to be maintained, or to worsen). Such diseases include, but are not limited to: macular degeneration, diabetic retinopathy, arthritis, obesity, psoriasis, eczema, and scleroderma. In addition, administration of FAS antagonists according to the methods of the invention can be used to treat and/or prevent blood vessel tumors, such as haemangiomas, angiosarcomas, and Kaposi's sarcoma.

Moreover, since tumors cannot grow beyond a volume of 2-3 mm$^3$ without recruiting an additional blood supply, administration of an FAS antagonist to inhibit angiogenesis provides a universal strategy for treating and/or preventing solid tumors that can otherwise exhibit widely different phenotypes Inhibition of angiogenesis by inhibiting FAS activity can also be used to prevent the metastatic spread of cancer, as infiltration of a tumor by blood vessels provides a route for tumor cells to enter the blood circulation and metastasize.

Examples of tumors that can be treated by administration of a FAS antagonist to inhibit tumor angiogenesis include, but are not limited to: tumors of the brain or nervous system (e.g., neuroblastoma, glioma, and glioblastoma), sarcomas (e.g., osteosarcoma, rhabdomyosarcoma, Ewing's sarcoma, angiosarcoma, Kaposi's sarcoma), lymphoma, and multiple myeloma. Other types of tumors that can be treated by administration of a FAS antagonist (e.g., a beta-lactone) to inhibit tumor angiogenesis include (but are not limited to): leukemias and carcinomas, e.g., carcinomas of the breast, prostate, ovary, endometrium, colon, stomach, liver, pancreas, esophagus, lung, oral mucosa, or skin.

Any beta-lactone, e.g., but not limited to, those examples described herein, can be used in the methods of the invention to inhibit angiogenesis in patients and subjects who would benefit from such inhibition. In addition, any other non-beta-lactone compound that inhibits FAS activity can be used as an anti-angiogenic factor in the methods of the invention. For example, the fungal compound cerulenin and its artificial derivative, c75 (Kuhajda et al. "Synthesis and antitumor activity of an inhibitor of fatty acid synthase." *Proc. Natl. Acad. Sci. U.S.A.* 97:3450-3454, 2000) can be used in the methods of the invention to inhibit FAS activity in order to inhibit angiogenesis and treat any disease or condition that involves pathological angiogenesis.

Beta-Lactone Compounds

The compounds of the invention and useful in all of the methods of the present invention are generally referred to as beta-lactones. Beta-lactones possess the core structure

where a number of different groups can be substituted for one or more hydrogen atoms of the —CH$_2$CH$_2$— unit present in the ring. For example, beta-lactones useful in the present invention are represented by formula I

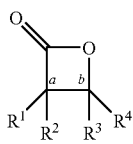

wherein $R^1$, $R^2$, $R^3$, and $R^4$ are, independently, hydrogen, an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group, or a combination thereof, and wherein the stereochemistry at carbons a and b is R or S.

Alternatively the beta lactones can have the formula VI:

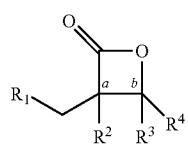

wherein $R^1$, $R^2$, $R^3$, and $R^4$ are, independently, hydrogen, an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group, or a combination thereof, and wherein the stereochemistry at carbons a and b is R or S, as described herein.

Variables such as $R^1$-$R^4$ used throughout the application are the same variables as previously defined unless stated to the contrary.

The term "alkyl group" is defined as a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like.

The term "alkenyl group" is defined as a hydrocarbon group of 2 to 24 carbon atoms and structural formula containing at least one carbon-carbon double bond.

The term "alkynyl group" is defined as a hydrocarbon group of 2 to 24 carbon atoms and a structural formula containing at least one carbon-carbon triple bond.

The term "halogenated alkyl group" is defined as an alkyl, alkenyl, or alkynyl group as defined above with one or more hydrogen atoms present on these groups substituted with a halogen (F, Cl, Br, I).

The term "aryl group" is defined as any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "cycloalkyl group" is defined as a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorous.

The term "aralkyl" is defined as an aryl group having an alkyl, alkynyl, or alkenyl group as defined above attached to the aromatic group. An example of an aralkyl group is a benzyl group.

The term "hydroxyl group" is represented by the formula —OH. The term "alkoxy group" is represented by the formula —OR, where R can be an alkyl, alkenyl, alkynyl, aryl, aralkyl, cycloalkyl, halogenated alkyl, or heterocycloalkyl group described above.

The term "hydroxyalkyl group" is defined as an alkyl, alkenyl, alkynyl, aryl, aralkyl, cycloalkyl, halogenated alkyl, or heterocycloalkyl group described above that has at least one hydrogen atom substituted with a hydroxyl group. The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

The term "amine group" is represented by the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide group" is represented by the formula —C(O)NRR', where R and R' can be an alkyl, alkenyl, alkynyl, aryl, aralkyl, cycloalkyl, halogenated alkyl, or heterocycloalkyl group described above.

The term "ester" is represented by the formula —OC(O)R, where R can be an alkyl, alkenyl, alkynyl, aryl, aralkyl, cycloalkyl, halogenated alkyl, or heterocycloalkyl group described above.

The term "carbonate group" is represented by the formula —OC(O)OR, where R can be an alkyl, alkenyl, alkynyl, aryl, aralkyl, cycloalkyl, halogenated alkyl, or heterocycloalkyl group described above.

The term "carboxylic acid" is represented by the formula —C(O)OH.

The term "aldehyde" is represented by the formula —C(O)H.

The term "keto group" is represented by the formula —C(O)R, where R is an alkyl, alkenyl, alkynyl, aryl, aralkyl, cycloalkyl, halogenated alkyl, or heterocycloalkyl group described above.

The term "carbonyl group" is represented by the formula C=O.

The term "ether group" is represented by the formula R(O)R', where R and R' can be, independently, an alkyl, alkenyl, alkynyl, aryl, aralkyl, cycloalkyl, halogenated alkyl, or heterocycloalkyl group described above.

The term "halide" is defined as F, Cl, Br, or I.

The term "urethane" is represented by the formula —OC(O)NRR', where R and R' can be, independently, an alkyl, alkenyl, alkynyl, aryl, aralkyl, cycloalkyl, halogenated alkyl, or heterocycloalkyl group described above.

The term "silyl group" is represented by the formula —SiRR'R", where R, R', and R" can be, independently, an alkyl, alkenyl, alkynyl, aryl, aralkyl, cycloalkyl, halogenated alkyl, alkoxy, or heterocycloalkyl group described above.

The term "sulfo-oxo group" is represented by the formulas —S(O)$_2$R, —OS(O)$_2$R, or, —OS(O)$_2$OR, where R can be an alkyl, alkenyl, alkynyl, aryl, aralkyl, cycloalkyl, halogenated alkyl, or heterocycloalkyl group described above.

R$^1$-R$^4$ can, independently, possess two or more of the groups listed above. For example, if R$^1$ is a straight chain alkyl group, one of the hydrogen atoms of the alkyl group can be substituted with a hydroxyl group, an alkoxy group, etc. Depending upon the groups that are selected, a first group may be incorporated within the second group or, alternatively, the first group may be pendant (i.e., attached) to the second group. For example, with the phrase "an alkyl group further including an ester group," the ester group may be incorporated within the backbone of alkyl group. Alternatively, the ester can be attached to the backbone of the alkyl group. The nature of the group(s) that is (are) selected will determine if the first group is embedded or attached to the second group.

The compounds represented by formula I can be optically active or racemic. The stereochemistry at carbons a and b can vary, and will depend upon the spatial relationship between R$^1$, R$^2$, R$^3$, and R$^4$ to one another. In one embodiment, the stereochemistry at carbons a and b is S. In another embodiment, the stereochemistry at carbons a and b is R. In a further embodiment, the stereochemistry at carbon a is S and the stereochemistry at carbon b is R. In a further embodiment, the stereochemistry at carbons a is R and the stereochemistry at carbon b is S. Using techniques known in the art, it is possible to vary the stereochemistry at carbons a and b.

In one embodiment, R$^1$ is an alkyl group. The alkyl group can be branched or straight chain. In one embodiment, R$^1$ is a straight chain C$_1$ to C$_{20}$, C$_3$ to C$_{18}$, C$_5$ to C$_{16}$, C$_7$ to C$_{14}$, or C$_9$ to C$_{12}$ alkyl group. In another embodiment, R$^1$ is a C$_1$ to C$_5$ alkyl group, such as methyl, ethyl, propyl, isopropyl, butyl, isobutyl, or tert-butyl.

In one embodiment, R$^3$ is a branched or straight chain C$_3$ to C$_{20}$, C$_5$ to C$_{18}$, C$_7$ to C$_{16}$, C$_9$ to C$_{14}$, or C$_{10}$ to C$_{12}$ alkyl group. Alternatively, R$^3$ is a branched or straight chain C$_3$ to C$_{20}$, C$_5$ to C$_{18}$, C$_7$ to C$_{16}$, C$_9$ to C$_{14}$, or C$_{10}$ to C$_{12}$ alkenyl group. The alkyl or alkenyl group of R$^3$ can be substituted with one or more of the following groups: an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, or a sulfo-oxo group. In a further embodiment, when R$^3$ is an alkyl or alkenyl group, the alkyl or alkenyl group comprises an ester group. The ester can optionally comprise any of the groups listed above. In one embodiment, the ester group further comprises an amide group.

In another embodiment, R$^3$ is a C$_3$ to C$_{20}$ alkenyl group comprising at least one hydroxyl group or at least one protected hydroxyl group. The term "protected hydroxyl group" refers to a hydroxyl group that has been converted to a group such as, but not limited to, an alkoxy group, an ester group, an aldehyde, a keto group, a carbonate, an amide, a silyl group, or a sulfo-oxo group. "*Protecting Groups in Organic Synthesis*" by T. W. Green, John Wiley and Sons, 1981, pp. 10-81, which is incorporated by reference, discloses numerous techniques for protecting a hydroxyl group. In another embodiment, when R$^3$ is an alkenyl group comprising at least one hydroxyl group or at least one protected hydroxyl group, R$^3$ further comprises a carbonyl group.

In one embodiment, R$^1$ is an alkyl group, R$^2$ and R$^4$ are hydrogen, R$^3$ is an alkyl group comprising an ester group, the stereochemistry at carbon a is S, and the stereochemistry at carbon b is S.

In another embodiment, R$^1$ is an alkyl group, R$^2$ and R$^4$ are hydrogen, R$^3$ is an alkenyl group comprising an ester group, the stereochemistry at carbon a is S, and the stereochemistry at carbon b is S.

In another embodiment, R$^1$ is an alkyl group, R$^2$ and R$^4$ are hydrogen, R$^3$ is an alkenyl group comprising at least one hydroxyl group or at least one protected hydroxyl group, the stereochemistry at carbon a is S, and the stereochemistry at carbon b is S.

In other embodiments, the beta-lactone is a compound provided below, which can be prepared using techniques known in the art:

(1S)-1-[(2S,3S)-3-hexyl-4-oxo-2-oxetanyl]tridecyl ester L-leucine

1-[(3-hexyl-4-oxo-2-oxetanyl)methyl]dodecyl ester L-leucine 3-hexyl-4-(2-hydroxytridecyl)-2-oxetanone (3S,4S)-3-hexyl-4-[(1S)-1-hydroxytridecyl]-2-oxetanone 1-[(3-hexyl-4-oxo-2-oxetanyl)methyl]dodecyl ester N-[(1,1-dimethylethoxy)carbonyl]-L-leucine 1-[(3-hexyl-4-oxo-2-oxetanyl)methyl]dodecyl ester N-benzoyl-L-Leucine 3-hexyl-4-(2-hydroxytridecyl)-2-oxetanone (2S,3R)-4-oxo-3-(4-pentenyl)-2-oxetanecarboxylic acid 1,1-dimethylethyl ester 3-hexyl-4-[2-(3-hydroxypropoxy)tridecyl]-2-oxetanone 4-[2-(3-chloropropoxy)tridecyl]-3-hexyl-2-oxetanone 1-[(3-hexyl-4-oxo-2-oxetanyl)methyl]dodecyl ester N-[4-(hydroxymethyl)benzoyl]-L-Leucine (2E,4E,7R)-11-[(2R,3R)-3-(hydroxymethyl)-4-oxo-2-oxetanyl]-3,5,7-trimethyl-2,4-undecadienal (3R,4R)-3-(phenylmethyl)-4-[(trimethylsilyl)ethynyl]-2-oxetanone (3R,4R)-4-[4-[(4-methoxyphenyl)methoxy-1]-1-butynyl]-3-methyl-2-oxetanone (3R,4R)-3-methyl-4-[3-(phenylmethoxy)-1-propynyl]-2-oxetanone L-alanyl-3-[(1R,2S)-2-[[[(2R,3S)-3-[(1S)-methylpropyl]-4-oxo-2-oxetanyl]carbonyl]amino]cyclopropyl]-L-alanine L-alanyl-N-5-[[(2R,3S)-3-[(1S)-1-methylpropyl]-4-oxo-2-oxetanyl]carbonyl]-L-ornithine N-[(1,1-dimethylethoxy)carbonyl]-L-alanyl-3-[(1R,2S)-2-[[[(2R,3S)-3-[(1S)-methylpropyl]-4-oxo-2-oxetanyl]carbonyl]amino]cyclopropyl]-L-alanine (1S)-1-[[(2S,3S)-3-hexyl-4-oxo-2-oxetanyl]methyl]hexyl ester N-formyl-L-valine 6-[(2-amino-5-chlorobenzoyl)amino]-2,4,6,7-tetradeoxy-2,4,4-trimethyl-,.beta.-lactone, L-ribo-5-Heptulosonic acid 6-[[2-(acetylamino)-5-chlorobenzoyl]amino]-2,4,6,7-tetradeoxy-2,4,4-trimethyl-L-ribo-5-heptulosonic acid beta-lactone

[3S-[3.alpha.,4.beta.(1R*,3E,5S*,7R*,8S*,9S*)]]-4-[8-(acetyloxy)-1,3,5,7,9-pentamethyl-6-oxo-3-undecenyl]-3-methyl-2-oxetanone

Figure 10:
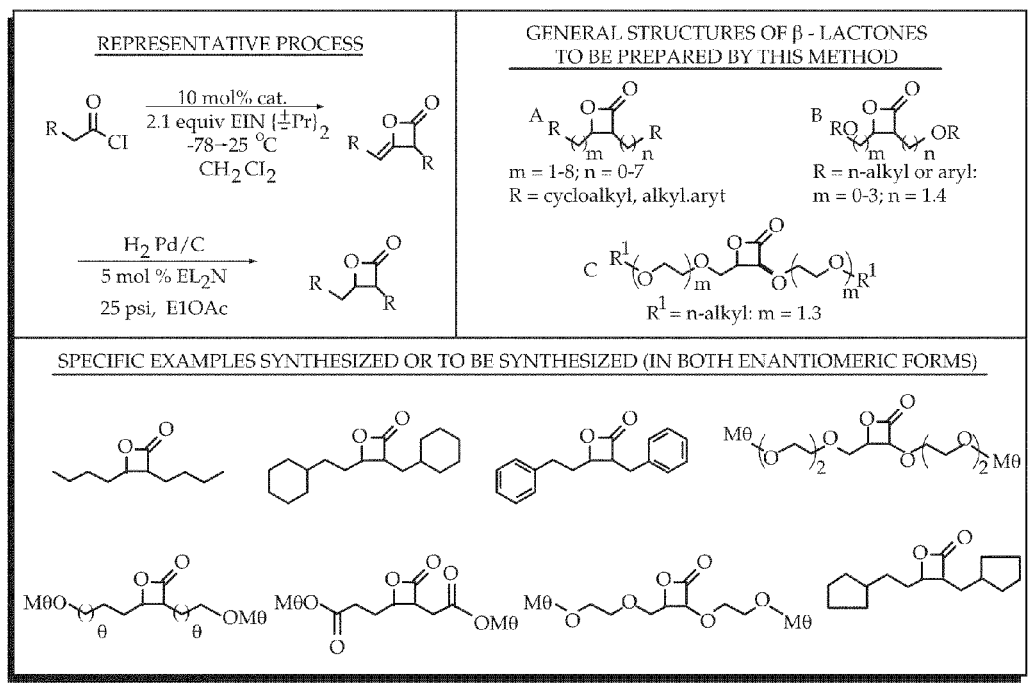
FIG. 10 illustrates the inventive method for preparing beta-lactones and illustrates the general structures and the specific structures synthesized using the inventive method.
Figure 11:
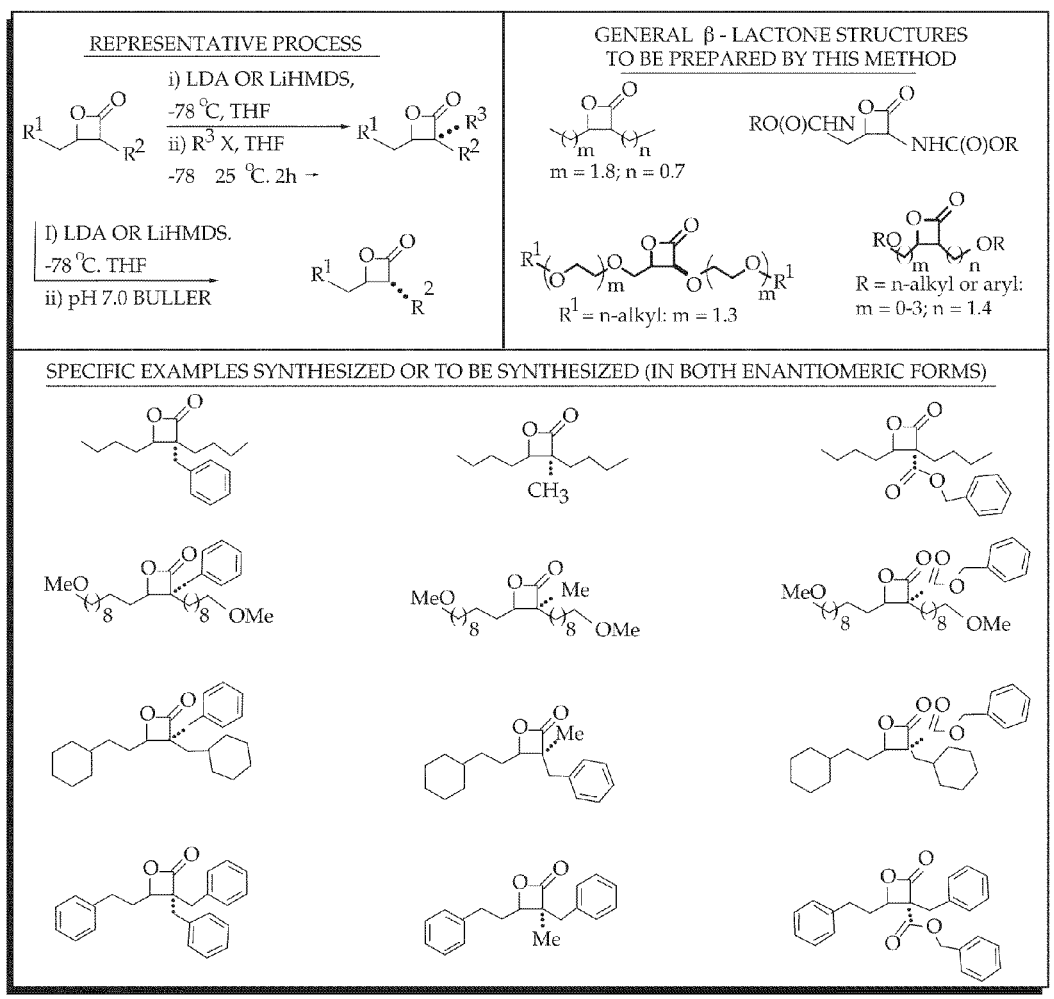
FIG. 11 illustrates epimerization and acylation/alkylation of the beta-lactones synthesized using the invention method. Further illustrated are the general structures and the specific structures synthesized hereby.
Figure 12:
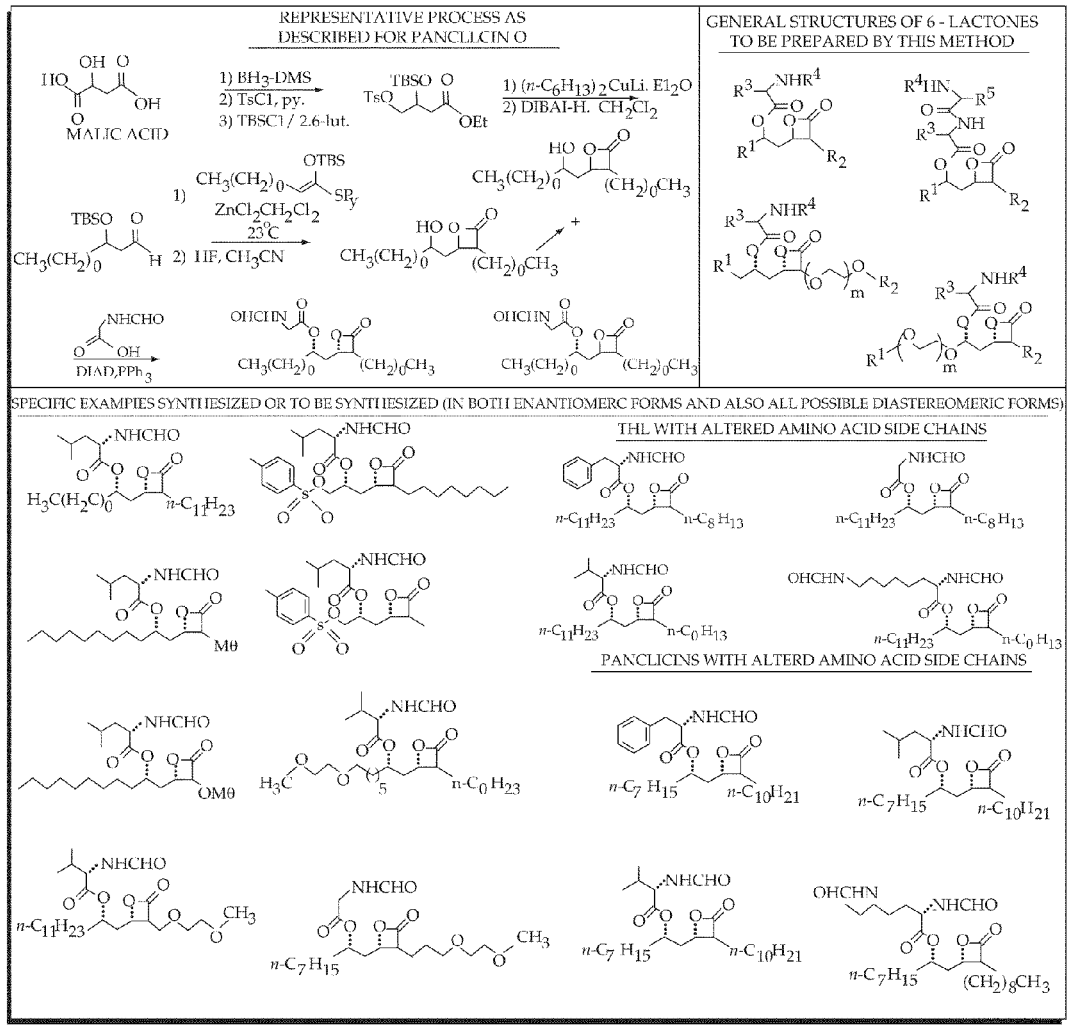
FIG. 12 illustrates use of the current invention method to prepare beta lactones that closely resemble tetrahydrolipstatin and panclicin D.

[3S-[3.alpha.,4.beta.(1R*,3E,5S*,7R*,8S*,9S*)]]-4-[8-(acetyloxy)-1,3,5,7,9-pentamethyl-6-oxo-3-undecenyl]-3-ethyl-2-oxetanone 4-(8-hydroxy-1,3,5,7,9-pentamethyl-6-oxoundecyl)-3-methyl-2-oxetanone (3S,4S)-3-hexyl-4-[(2R)-2-hydroxytridecyl]-2-oxetanone (3S,4S)-3-hexyl-4-[(2R)-2-[[tris(1-methylethyl)silyl]oxy]tridecyl]-2-oxetanone (3S,4S)-3-(2-hexenyl)-4-[(2-undecyl-1,3-dioxolan-2-yl)methyl]-2-oxetanone
(3S,4S)-3-(2-hexenyl)-4-(2-oxotridecyl)-2-oxetanone
(4S)-3-3-di-2-hexenyl-4-[(2-undecyl-1,3-dioxolan-2-yl)methyl]-2-oxetanone
L-alanyl-3-[(1R,2S)-2-[[[(2R,3S)-3-[(1S)-1-methylpropyl]-4-oxo-2-oxetanyl]carbonyl]amino]cyclopropyl]-L-alanine
(1S)-1-[[(2S,3S)-3-hexyl-4-oxo-2-oxetanyl]methyl]dodecyl ester N-[(phenylmethoxy)carbonyl]-L-leucine
(3S,4S)-3-hexyl-4-[(2S)-2-[tetrahydro-2H-pyran-2-yl)oxy]tridecyl]-2-oxetanone
4-nonyl-3-[8-(phenylmethoxy)octyl]-2-oxetanone
3-(8-hydroxyoctyl)-4-nonyl-2-oxetanone
(2E,4E,7R)-11-[(2R,3R)-3-ethenyl-4-oxo-2-oxetanyl]-3,5,7-trimethyl-2,4-Undecadienoic acid diphenylmethyl ester
(2E)-3-[3-[(2R)-6-[(2R,3R)-3-ethenyl-4-oxo-2-oxetanyl]-2-methylhexyl]-3-methyloxiranyl]-2-butenoic acid diphenylmethyl ester
(2E)-3-[3-[(2R)-6-[(2R,3R)-3-(hydroxymethyl)-4-oxo-2-oxetanyl]-2-methylhexyl]-3-methyloxiranyl]-2-butenoic acid diphenylmethyl ester
(2E,4E,7R)-11-[(2R,3R)-3-(hydroxymethyl)-4-oxo-2-oxetanyl]-3,5,7-trimethyl-2,4-undecadienoic acid diphenylmethyl ester
(1S)-1-[[(2S,3S)-3-decyl-4-oxo-2-oxetanyl]methyl]octyl ester N-formyl-glycine
(3S,4S)-4-[(2R)-2-hydroxynonyl]-3-(8-methylnonyl)-3-(trimethylsilyl)-2-oxetanone
(3S,4S)-,3-dodecyl-4-[(2R)-2-hydroxynonyl]-3-(trimethylsilyl)-2-oxetanone
(3R,4S)-3-decyl-4-[(2R)-2-hydroxynonyl]-2-oxetanone
[3S-[3.alpha.,4.beta.(S*)]]-3-decyl-4-(2-hydroxynonyl)-2-oxetanone
(3R,4S)-4-[(2R)-2-[[(1,1-dimethylethyl)dimethylsilyl]oxy]nonyl]-3-(8-methylnonyl)-3-(trimethylsilyl)-2-oxetanone
(3S,4S)-4-[(2R)-2-[[(1,1-dimethylethyl)dimethylsilyl]oxy]nonyl]-3-(8-methylnonyl)-3-(trimethylsilyl)-2-oxetanone
(3R,4S)-4-[(2R)-2-hydroxynonyl]-3-(8-methylnonyl)-3-(trimethylsilyl)-2-oxetanone
(3S,4S)-4-[(2R)-2-hydroxynonyl]-3-(8-methylnonyl)-2-oxetanone
(1S)-1-[[(2S,3S)-3-(8-methylnonyl)-4-oxo-2-oxetanyl]methyl]octyl ester N-(triphenylmethyl)-L-alanine
(3R,4S)-3-decyl-4-[(2R)-2-[[(1,1-dimethylethyl)dimethylsilyl]oxy]nonyl]-3-(trimethylsilyl)-2-oxetanone
(3S,4S)-3-decyl-4-[(2R)-2-[[(1,1-dimethylethyl)dimethylsilyl]oxy]nonyl]-3-(trimethylsilyl)-2-oxetanone
[3S-[3.alpha.,4.beta.(S*)]]-3-decyl-4-(2-hydroxynonyl)-2-oxetanone
[3S-[3.alpha.,4.beta.(S*)]]-3-decyl-4-[2-[[(1,1-dimethylethyl)dimethylsilyl]oxy]nonyl]-2-oxetanone
[3S-[3-.alpha.,4.beta.(S*)]]-3-decyl-4-(2-hydroxynonyl)-2-oxetanone
(3R,4R)-3-methyl-4-(2-phenylethyl)-2-oxetanone
4-heptyl-3,3-dimethyl-2-oxetanone
trans-4-cyclohexyl-3,4-dimethyl-2-oxetanone
[2R-[2.alpha.(2E,4E),3.beta.]]-11-[3-(hydroxymethyl)-4-oxo-2-oxetanyl]-3,5,7-trimethyl-2,4-undecadienoic acid methyl ester
(1S)-1-[[(2S,3S)-3-(8-methylnonyl)-4-oxo-2-oxetanyl]methyl]octyl ester N-formyl-glycine
(1S)-1-[[(2S,3S)-3-decyl-4-oxo-2-oxetanyl]methyl]octyl ester N-formyl-glycine
(1S)-1-[[(2S,3S)-3-decyl-4-oxo-2-oxetanyl]methyl]octyl ester N-formyl-L-alanine
[3R-[3.alpha.4.beta.(*)]]-3-[[[(1,1,-dimethylethyl)diphenylsilyl]oxy]methyl]-4-(5-methyl-7-oxooctyl)-2-oxetanone
trans-4-oxo-3-[(triphenylmethoxy)methyl]-2-oxetaneundecanoic acid methyl ester
trans-3-(hydroxymethyl)-4-oxo-2-oxetaneundecanoic acid
(2S-trans)-N,N-diethyl-3-hexyl-4-oxo-2-oxetanepentanamide
N-formyl-, 4-(3-hexyl-4-oxo-2-oxetanyl)butyl ester, (2S-trans)-, L-Leucine
(3S-trans)-3-hexyl-4-(4-hydroxybutyl)-2-oxetanone
[2R-[2.alpha.(2E,4E,7R*),3.beta.]]-3,5,7-trimethyl-11-[4-oxo-3-[(triphenylmethoxy)methyl]-2-oxetanyl]-2,4-undecadienoic acid methyl ester
[3.alpha.(E),4.alpha.]-3-(1,3-butadienyl)-3-methyl-4-pentyl-2-oxetanone
[3.alpha.(E),4.beta.]-3-(1,3-butadienyl)-3-methyl-4-pentyl-2-oxetanone
[2R-[2.alpha.(2E,4E,7R*),3.beta.]]-11-[3-(methoxymethyl)-4-oxo-2-oxetanyl]-3,5,7-trimethyl-2,4-undecadienoic acid methyl ester
[2R-[2.alpha.(2E,4E),3.beta.]]-11-[3-(hydroxymethyl)-4-oxo-2-oxetanyl]-3,5,7-trimethyl-2,4-undecadienoic acid methyl ester
[3.alpha.,4.beta.(1R*,3E,5S*,7R*,8R*)]-4-[8-[[(1,1-dimethylethyl)dimethylsilyl]oxy]-1,3,5,7-tetramethyl-9-methylene-6-oxo-3-undecenyl]-3-methyl-2-oxetanone
[3.alpha.,4.beta.(1R*,3E,5S*,7R*,8R*)]-4-[8-hydroxy-1,3,5,7-tetramethyl-9-methylene-6-oxo-3-undecenyl]-3-methyl-2-oxetanone
[3.alpha.,4.beta.(1R*,3E,5S*,7R*,8S*,9R*)]-4-[8-hydroxy-1,3,5,7,9-pentamethyl-6-oxo-3-undecenyl]-3-methyl-2-oxetanone
1-[(3-fluoro-3-hexyl-4-oxo-2-oxetanyl)methyl]dodecyl ester N-formyl-L-leucine
[2S-[2.alpha.(R*),3.alpha.]]-1-[(3-fluoro-3-hexyl-4-oxo-2-oxetanyl)methyl]dodecyl ester N-formyl-L-leucine
[3R-[3.alpha.,4.beta.(R*)]]-3-(hydroxymethyl)-4-(5-methyl-7-oxooctyl)-2-oxetanone
[3S-[3.alpha.,4.beta.(2S*,5Z)]]-3-hexyl-4-(2-hydroxy-5-tridecenyl)-2-oxetanone
4-[8-(acetyloxy)octyl]-3-(1-methyl-2-propenyl)-2-oxetanone
(3R,4S)-3-butyl-4-pentyloxetan-2-one
(3R,4R)-3-butyl-4-pentyloxetan-2-one
(3R,4S)-3-butyl-3-methyl-4-pentyloxetan-2-one
(3S,4S)-3-benzyl-3-butyl-4-pentyloxetan-2-one
(3S,4S)-benzyl-3-butyl-2-oxo-4-pentyloxetane-3-carboxylate As well as the compounds shown in FIGS. 10, 11 and 12.

In another embodiment, the beta-lactones disclosed in International Publication No. WO 200004300, Japanese Publication No. 03115274, European Publication No. 185359 A2, and U.S. Pat. Nos. 4,931,463, 5,175,186, 5,246,960, 4,873,260, 4,806,564, 4,983,746, 5,260,310, 5,376,674, 5,466,708, and 5,399,720, which are incorporated by reference in their entireties, are useful in the invention.

In one embodiment, the compound having the formula I is tetrahydrolipstatin, which is also referred to as orlistat. The structure of tetrahydrolipstatin is depicted in formula II. In another embodiment, the compound is lipstatin, which is depicted in formula III. The synthesis of tetrahydrolipstatin and lipstatin is disclosed in U.S. Pat. No. 4,598,089, which is incorporated by reference.

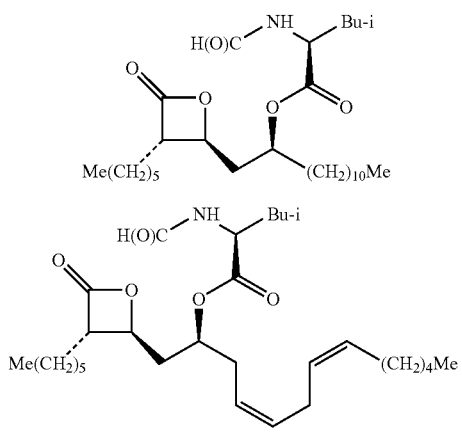

In another embodiment, the compound having the formula I is ebelactone A and B, which are depicted in formulas IV and V, respectively. The synthesis of ebelactone A and B is disclosed in the journal article by Paterson and Hulme entitled "*Total Synthesis of (−)-Ebelactone A and B*" *J. Org. Chem.*, 1995, 60(11), 3288-3300, which is incorporated by reference in its entirety.

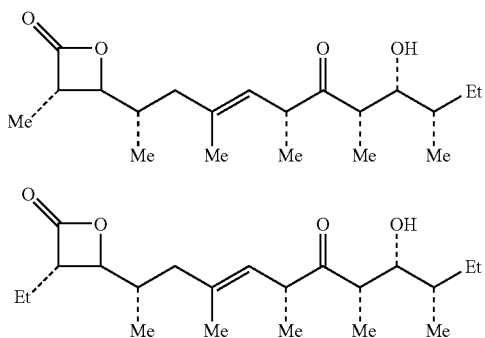

Methods of Administration of Beta-Lactones and Other Inhibitors of Fatty Acid Synthase Activity The FAS antagonists for use in the methods of the invention can be administered to subjects with a pharmaceutically acceptable diluent, carrier, or excipient, in unit dosage form. By "pharmaceutically acceptable" is meant a material that is not biologically or otherwise undesirable, i.e., the material may be administered to an individual along with an FAS antagonist without causing any undesirable biological effects or interacting in a deleterious manner with any of the components of the pharmaceutical composition in which it is contained. Conventional pharmaceutical practice may be employed to provide suitable formulations or compositions to administer such compositions to subjects. Any appropriate route of administration may be employed, for example, but not limited to, intravenous, parenteral, transcutaneous, subcutaneous, intramuscular, intracranial, intraorbital, ophthalmic, intraventricular, intracapsular, intraspinal, intracisternal, intraperitoneal, intranasal, intrarectal, intravaginal, aerosol, or oral administration. Therapeutic formulations may be in the form of liquid solutions or suspensions; for oral administration, formulations may be in the form of tablets or capsules; for intranasal formulations, in the form of powders, nasal drops, or aerosols; for intravaginal formulations, vaginal creams, suppositories, or pessaries; for transdermal formulations, in the form of creams or distributed onto patches to be applied to the skin.

Methods well known in the art for making formulations are found in, for example, *Remington: The Science and Practice of Pharmacy* (19th ed.) ed. A. R. Gennaro, Mack Publishing Company, Easton, Pa. 1995. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for molecules of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Any beta-lactone or other compound of the invention can be administered singly or in combination. In just example, tetrahydrolipostatin can be administered by itself or in combination with ebelactone A and/or B, and/or in combination with another compound that inhibits FAS.

Dosage

The beta-lactones and other FAS antagonists for use in the methods of the invention may be administered to a subject in an effective amount, i.e., amount sufficient to partially or fully inhibit FAS activity in a subject in need thereof, e.g., to treat a cancer or to inhibit angiogenesis in a subject in need of such treatment. One of ordinary skill in the art will understand that the optimal dosage used will vary according to the individual being treated and the particular cancer, disease, or other condition for which the individual is being treated, the particular compound being used, and the chosen route of administration. The optimal dosage will also vary among individuals on the basis of age, size, weight, gender, and physical condition. Methods for determining optimal dosages are described, for example, in *Remington: The Science and Practice of Pharmacy* (19th ed.) ed. A. R. Gennaro, Mack Publishing Company, Easton, Pa. 1995. Typically, a pharmaceutically effective dosage would be between about 0.001 and 200 mg/kg body weight of the subject to be treated.

Efficacy

The efficacy of administration of a particular dose of a beta-lactone or other FAS antagonist according to the methods of the invention can be determined by evaluating the particular aspects of the medical history, signs, symptoms, and objective laboratory tests that are known to be useful in evaluating the status of a subject in need of inhibition of FAS for the treatment of cancer or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: 1) a subject's physical condition is shown to be improved (e.g., a tumor has partially or fully regressed), 2) the progression of the disease or condition is shown to be stabilized, or slowed, or reversed, or 3) the need for other medications for treating the disease or condition is lessened or obviated, then a particular treatment regimen will be considered efficacious.

Identification of Compounds that Inhibit FAS Activity

In general, compounds that inhibit the activity of FAS (i.e., beta-lactones and other FAS antagonists) can be identified from libraries of natural products or synthetic (or semi-synthetic) extracts or chemical libraries according to methods known in the art and/or described herein. Such screening methods include (but are not limited to): serine hydrolase activity-profiling assays, [$^{14}$C]-acetate incorporation assays, cell proliferation assays, apoptosis assays, and/or angiogenesis assays (see, e.g., Salcedo et al. "Human endothelial cells express CCR2 and respond to MCP-1: direct role of MCP-1 in angiogenesis and tumor progression." *Blood* 96:34, 40, 2000). Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds (e.g., but not limited to, antibodies, peptides, and aptamers). Synthetic compound libraries are commercially available, e.g., from Brandon Associates (Merrimack, N.H.) and Aldrich Chemical (Milwaukee, Wis.).

Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

In sum, a test compound for use in the assay methods of the invention can be any molecule, be it naturally-occurring or artificially-derived, that is surveyed for its ability to: inhibit the activity of fatty acid synthase, inhibit angiogenesis or a disease that involves pathogenic angiogenesis, inhibit cell proliferation, promote apoptosis, and/or promote cell cycle arrest.

Samples for use in the assay methods of the invention include any specimen that can be tested for fatty acid synthase activity and/or that can be used to identify compounds that inhibit fatty acid synthase, inhibit angiogenesis or a disease that involves pathogenic angiogenesis, inhibit cell proliferation, promote apoptosis, and/or promote cell cycle arrest. Examples include, but are not limited to: a sample from a patient or subject, such as a cell, tissue, or tumor sample; a cell (e.g., a prokaryotic or eukaryotic cell that expresses endogenous or recombinant FAS); a lysate (or lysate fraction) or extract derived from a cell; or a molecule derived from a cell or cellular material.

Those skilled in the art of drug discovery and development readily understand that methods for de-replication (e.g., taxonomic de-replication, biological de-replication, and chemical de-replication, or any combination thereof) or the elimination of replicates or repeats of materials already known for their effect on FAS should be employed whenever possible.

When a crude extract is found to have a desired activity, further fractionation of the positive lead extract is necessary to isolate chemical constituents responsible for the observed effect. Thus, the goal of the extraction, fractionation, and purification process is the careful characterization and identification of a chemical entity within the crude extract that inhibits FAS activity. The same assays for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using in vitro assays (e.g., for cell cycle arrest, apoptosis, and/or angiogenesis) and in vivo animal models for diseases, conditions, and/or biological processes (e.g., cancer, angiogenesis, or a disease involving pathological angiogenesis) in which it is desirable to inhibit FAS activity to treat or prevent the disease or condition.

EXAMPLES

The present invention is more particularly described in the following examples, which are intended as illustrative only since numerous modifications and variations thereof will be apparent to those of ordinary skill in the art.

Example I

Orlistat and Ebelactones A and B Inhibit Fatty Acid Synthase Activity and Induce Selective Apoptosis of Prostate Tumor Cells Recent work in the area of chemical biology points the way toward direct profiling of protein activity. Two groups have shown it possible to create chemical probes that react at the active site of multiple enzymes of a given class. Liu et al showed how to obtain the profile of serine hydrolase activity with a probe containing fluorophosphonate as the warhead and biotin as the reporter (Liu et al. "Activity-based protein profiling: the serine hydrolase." *Proc. Natl. Acad. Sci. U.S.A* 96:14694-9, 1999). In a related approach, Bogyo's group showed that the family of cysteine proteinases could be tagged covalently with reactive epoxides (Greenbaum et al. "Epoxide electrophiles as activity-dependent cysteine protease profiling and discovery tools" *Chem. Biol.* 7:569-81, 2000). Because activity-based probes bind at the active site of an enzyme, a direct measure of the level of active enzyme can be obtained, and it becomes possible to use straightforward competition assays to screen for inhibitors.

The present study employs such an approach. An activity-based profiling effort was coupled to a simultaneous screen for antagonists of serine hydrolases in prostate cancer cells. This was accomplished with an activity-based probe comprised of a fluorophosphonate warhead linked to the tetramethyl rhodamine fluorophore (FP-TAMRA) (Patricelli et al. "Direct visualization of serine hydrolase activities in complex proteomes using fluorescent active site-directed probes." *Proteomics* 1:1067-1071, 2001).

FIG. 1 is a scan of an SDS-polyacrylamide gel showing an activity profiling experiment for normal and neoplastic prostate epithelial cells. Lysates were generated from primary cultures of normal prostatic epithelial cells (PrEC), and from three prostate tumor cell lines (LNCaP, DU-145, and PC-3). Lysates (40 μg of total protein, at a concentration of 1 mg/ml) were incubated with FP-PEG-TAMRA (2 μM) for one hour at room temperature. Reactions were stopped by the addition of SDS-PAGE loading buffer containing β-mercaptoethanol and boiling. Non-specific labeling with the probe activity was measured in samples that were boiled prior to the addition of fp-PEG-TAMRA (lanes marked +). Samples were resolved by 10% SDS-PAGE and visualized at 605 nm using a Hitachi flat bed gel scanner (lanes 1-8). The effect of three beta-lactones on the activity-labeling of serine hydrolases from PC-3 cells was assessed in a similar manner. Prior to incubation with FP-PEG-TAMRA, lysates (40 μg) were pre-incubated for 30 min with 100 μM of ebelactone A (lane 10), ebelactone B (lane 11), or orlistat (lane 12). Following labeling with FP-PEG-TAMRA the reactions were halted and enzyme activity visualized as described above.

For each cell line tested as described above, approximately fifteen different hydrolases were visualized as fluorescent bands on SDS gels. The pattern of serine hydrolase expression was generally similar among the cell lines, with two significant distinctions. A hydrolase with a mass of approximately 270 kDa was expressed in an of the tumor lines, but was absent in normal PrECs. Peptide mass fingerprinting with mass spectrometry showed this band to be fatty acid synthase (FAS), an observation that was confirmed by immunoprecipitating the complex between FP-TAMRA and FAS.

As the single eukaryotic enzyme capable of synthesizing palmitate, FAS is responsible for generating the precursor for the majority of cellular fatty acids. FAS has a unique structure and mode of action. The enzyme contains six separate enzymatic pockets along with an acyl carrier protein. Palmitate is generated by the enzymes repeated condensation of acetyl co-A and malonyl co-A. Seven such condensation cycles yield the sixteen-carbon polyunsaturated fatty acid palmitate. Palmitate remains covalently attached to the acyl carrier protein of the enzyme until it is liberated by the final enzymatic pocket on the enzyme, the intrinsic thioesterase. This thioesterase is the sole serine hydrolase within FAS, and is targeted by FP-TAMRA.

FAS is known to be up-regulated in a wide range of tumors, and its function has been strongly linked to tumor cell proliferation, making it an attractive therapeutic target for cancer. We capitalized on the fact that FP-TAMRA reacts with the active site of all of the serine hydrolases visualized in FIG. 1 to a selectively identify an inhibitor of the FAS thioesterase domain.

Three beta-lactones, all derivatives of natural products, were tested for the ability to block activity-based labeling of FAS. Interestingly, all three compounds had the ability to inhibit the thioesterase of FAS, but only tetrahydrolipstatin selectively inhibited FAS. Tetrahydroliptstatin, also known as orlistat, is a drug that has already been approved for weight management in obese patients. Interestingly however, the effectiveness of orlistat in this indication is connected to its ability to inhibit pancreatic lipase in the gastrointestinal tract, thereby preventing uptake of dietary fat. Such inhibition occurs following nucleophilic attack by the active site serine on the carbonyl carbon of the lactone ring. The reaction yields a covalent adduct between enzyme and inhibitor (Hadvary et al. "The lipase inhibitor tetrahydrolipstatin binds covalently to the putative active site serine of pancreatic lipase." *J. Biol. Chem.* 266:2021-7, 1991). The inhibition of FAS by orlistat has never been reported, and is not believed to be relevant to its mode of action in weight loss.

Figure 2:
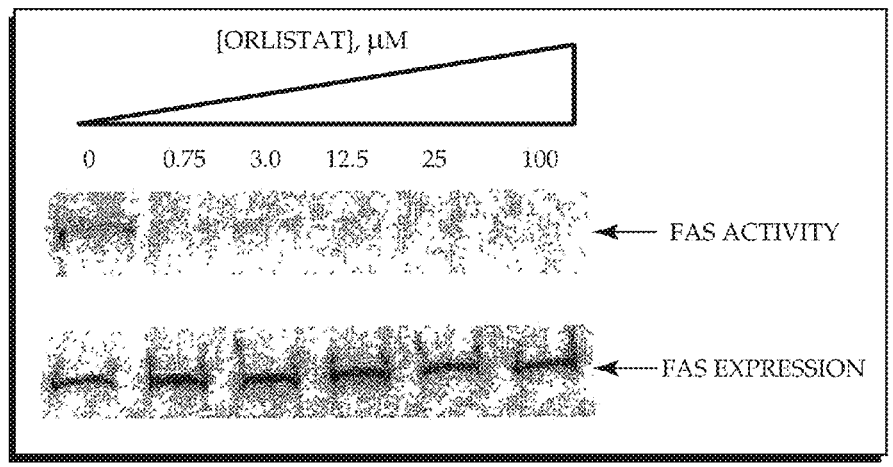
FIG. 2 shows a scan of an SDS-polyacrylamide gel (top panel) that indicates that the labeling of fatty acid synthase (FAS) by FP-Bodipy is inhibited in tetrahydrolipstatin-treated cells, and a scan of a Western blot (bottom panel) that shows that the FAS expression levels are similar in the various samples.

Studies were performed to determine the effect of orlistat on tumor cells. As a first step, we measured the ability to inhibit the activity of FAS in whole cells. PC-3 cells treated with a concentration range of orlistat for one hour were incubated with a membrane-permeable activity-based probe, FP-Bodipy (2 μM), for an additional hour, and the labeled cells were harvested and visualized as described above. A concentration-dependent inhibition of labeling by FP-Bodipy was evident (FIG. 2; top panel), indicating enzyme inhibition. These effects were independent of the abundance of FAS, which was measured from the same treated samples by Western blot (FIG. 2; bottom panel). The effects of orlistat on cellular fatty acid synthesis were measured by assessing the incorporation of [$^{14}$C]-acetate into fatty acids. A level of orlistat capable of inhibiting about 90% of the activity-based labeling of FAS reduced total cellular fatty acid synthesis by approximately 70%.

The effects of orlistat were not limited to inhibition of fatty acid synthesis. This effect apparently has dramatic downstream consequences, because orlistat induced a pronounced apoptotic response in the DU-145 and PC3 cells, which are the two more differentiated prostate lines. A small apoptotic response was observed in the LNCap cells, which are less differentiated and which retain androgen responsiveness. Orlistat has no apoptotic effect on normal prostate epithelial (PrEC) cells, nor on a series of normal human fibroblasts.

Methods

Profiling serine hydrolase activity in prostate cell lines. The LNCaP, DU-145 and PC-3 cell lines (ATCC, Rockville, Md.) were maintained in RPMI 1640 (Irvine Scientific, Santa Ana, Calif.) supplemented with 10% fetal bovine serum at 37° C. in 5% $CO_2$. The PrEC cell line (Clonetics, Walkerville, Md.) was maintained according to the suppliers instructions. Each cell line was maintained in 150-mm tissue culture dishes. To generated protein lysates, cells were washed with ice-cold phosphate buffered saline (PBS) and harvested by scraping with a cell lifter into cold PBS. Cells were collected by centrifugation and the pellets were resuspended in 50 mM Tris-Cl, pH 8.0. Lysis was accomplished by sonication and Dounce-homogenization as described previously (Liu et al., supra; and Kidd et al. "Profiling Serine Hydrolase Activities in Complex Proteomes." *Biochemistry* 40:4005-4015, 2001). The soluble and insoluble cell fractions were separated by ultracentrifugation for one hour at 64,000 rpm at 4° C. Protein concentrations of the soluble fraction was determined by BCA assay (Pierce, Rockford, Ill.) versus a standard concentration of bovine serum albumin (BSA).

The serine hydrolase activity profiles of the prostate cell lines were measured using the fluorophosphonate probe fp-PEG-Tamra using methods described previously (Liu et al., supra; and Kidd et al., supra). Briefly, 40 μl of a 1 mg/ml solution of the soluble fractions of each cell lines were treated with 2 μM fp-PEG-Tamra for one hour at ambient temperature. The labeling reactions were stopped by the addition of Laemmli buffer followed by boiling for 5 minutes. As a control for non-specific reaction of the probe, a duplicate sample was boiled for ten minutes prior to labeling with fp-PEG-Tamra to denature all enzymatic activity. The labeled samples were resolved by 10% SDS-PAGE and visualized by scanning with a Hitachi flatbed scanner at 605 nm.

Alternatively, serine hydrolase activity in whole cells was measured with fp-Bodipy-Fl. Cells were plated in 24-well plates and the probe was added to a final concentration of 2 μM and labeled for one hour. The cells were lysed by the addition of Laemmli sample buffer followed by boiling. The labeled samples were resolved by 10% SDS-PAGE and visualized by scanning with a Hitachi flatbed scanner at 505 nm.

Inhibition of serine hydrolase activity with beta-lactone compounds. Ebelactone A and B stocks were made in DMSO. Orlistat was made in EtOH. Cell lysate were generated at 1 mg/ml as described above. Samples (40 μg) were incubated with inhibitors for twenty minutes prior to addition of fp-PEG-TAMRA. The final concentration of DMSO or EtOH in each reaction was 10%. The labeling reactions were stopped by the addition of Laemmli sample buffer and samples were resolved on 10% SDS-PAGE and visualized as described above.

Purification of serine hydrolases by avidin-biotin affinity chromatography. Serine hydrolases were purified from 2.5 mg of soluble cell lysates by avidin-biotin affinity chromatography (Liu et al., supra; and Kidd et al., supra). The lysates were pre-treated with avidin-agarose to remove non-specific binders. Lysates were labeled with fp-PEG-biotin (5 µM) for one hour at room temperature. Protein was separated from unincorporated fp-PEG-biotin by passage over a Nap 25 column. Protein containing fractions were pooled and SDS was added to a concentration of 0.5% and boiled for ten minutes. After boiling the samples were diluted with 50 mM Tris, pH 7.5 and 150 mM NaCl. Avidin-agarose was added to the solution for a one-hour incubation at room temperature. The agarose beads were pelleted by centrifugation and washed eight times with 50 mM Tris, ph 7.5, 150 mM NaCl and 1% Tween 20. Labeled protein was eluted by the addition of Laemmli buffer containing 1% SDS and boiling for ten minutes. Protein was resolved by 10% SDS-PAGE and detected by silver staining. Specific bands were extracted and subjected to in-gel trypsin digests and MALDI-TOF analysis as described previously (Landry et al. "A Method for Application of Samples to Matrix-Assisted Laser Desorption Ionization Time-of-Flight Targets That Enhances Peptide Detection." *Anal. Biochem.* 279:1-8, 2000; Harvey et al. "Insights into a plasma membrane signature." *Physiol. Genomics.* 5:129-136, 2001).

Detection of fatty acid synthase by Western blot. PC-3 cells ($5 \times 10^4$) were seeded in 24 well plates. Following treatment with orlistat, cells were collected, suspended in Laemmli sample buffer and boiled. Protein was resolved by 10% SDS-PAGE and transferred to nitrocellulose. The membrane was blocked with non-fat milk and probed with an anti-FAS monoclonal antibody (mAb) (Pharmingen, San Diego, Calif.) followed by horseradish peroxidase (HRP)-labeled rabbit anti-mouse IgG (BioRad, Hercules, Calif.) and chemiluminescence detection with Western Lighting Chemiluminescence Reagent (Perkin-Elmer, Boston, Mass.).

Inhibition of fatty acid synthesis by orlistat. Fatty acid synthesis in cells was measured by [$^{14}$C]-acetate incorporation (Kuhajda et al. "Fatty acid synthesis: a potential selective target for antineoplastic therapy." *Proc. Nat. Acad. Sci. U.S.A.* 91:6379-83, 1994; Pizer et al. "Pharmacological inhibitors of mammalian fatty acid synthase suppress DNA replication and induce apoptosis in tumor cell lines." *Cancer Res.* 58:4611-5, 1998). Cells were seeded at density of $2.5 \times 10^4$ cells/well in 24-well plates. Prior to the addition of orlistat, the wells were washed twice with PBS. Serum-free RPMI containing 300 µg/ml BSA and insulin/transferrin/selenium supplement was added to the wells, with or without orlistat. The cells were incubated for two hours prior to the addition of 1 µCi of [$^{14}$C]-acetate to label newly synthesized fatty acids. After two hours, the labeling medium was removed and the cells were washed with PBS/EDTA and trypsinized. The cells pellets were washed twice more with PBS and fatty acids were extracted by the addition of an equal mixture of chloroform-methanol for 30 minutes. The extracted material was dried under a stream of $N_2$ gas and extracted further with water-saturated butanol. The butanol was removed by drying under a stream of $N_2$ gas and labeled fatty acids were detected by scintillation counting.

Detection of orlistat-induced apoptosis by annexin V labeling. Three prostate cancer cell lines (LNCaP, DU-145 and PC-3) and human fibroblasts (HF) were seeded in 35 mm plates. The cells were washed twice with PBS and serum-free medium supplemented with 300 µg/ml BSA (Sigma, St. Louis, Mo.) and insulin/transferrin/selenium cocktail (Life Technologies, Rockville, Md.) containing various concentrations of orlistat was added. At various time points, the cells were harvested by trypsinization and washed twice with PBS. Cells were suspended at $1 \times 10^6$ cells/ml in annexin V incubation buffer (BioVision, Inc., Mountain View, Calif.) and treated with annexin V-FITC and propidium iodide. Apoptotic cells were quantified by fluorescence-activated cell sorting (FACS) analysis.

Example II

Orlistat Inhibits FAS Activity and Induces Cell Cycle Arrest and Apoptosis in Mammary Carcinoma Cells This study focused on the identification of serine hydrolases active in mammary carcinoma. Activity-based protein profiling was combined with a screen for small molecule antagonists to gain insight into the function of these hydrolases. One of the prominent serine hydrolases, fatty acid synthase, was found to be inhibited by tetrahydrolipstatin, a drug commonly referred to as orlistat. Surprisingly, in mammary carcinoma cells, orlistat elicits cell cycle arrest at the $G_1/S$ boundary. In more differentiated tumor cells, apoptosis soon follows. These experiments show the relevance of fatty acid synthase as a therapeutic target and link fatty acid synthesis to control of common cell cycle checkpoints. The study also reveals an unappreciated anti-tumor activity for orlistat, a drug approved for weight management in obesity.

Methods

Profiling Serine Hydrolase Activity in Mammary Epithelial Cells.

Primary human mammary endothelial cells (HMECs) and MCF-7, MDA-MB-231, and MDA-MB-435 cell lines (ATCC, Rockville, Md.) were maintained in RPMI 1640 (Irvine Scientific, Santa Ana, Calif.) supplemented with 10% fetal bovine serum at 37° C. in 5% $CO_2$. Each cell line was maintained in 150-mm tissue culture dishes. To generated protein lysates, cells were washed with ice-cold phosphate buffered saline (PBS) and harvested by scraping with a cell lifter into cold PBS. Cells were collected by centrifugation and the pellets were resuspended in 50 mM Tris-Cl, pH 8.0. Lysis was accomplished by sonication and Dounce homogenization as described previously (Liu et al. "Activity-based protein profiling: the serine hydrolase." *Proc. Natl. Acad. Sci. U.S.A* 96:14694-9, 1999; Kidd et al. "Profiling Serine Hydrolase Activities in Complex Proteomes." *Biochemistry* 40:4005-4015, 2001). The soluble and insoluble cell fractions were separated by ultracentrifugation for one hour at 64,000 rpm at 4° C. Protein concentrations of the soluble fraction was determined by BCA assay (Pierce, Rockford, Ill.) versus a standard concentration of bovine serum albumin (BSA).

The serine hydrolase activity profiles of the prostate cell lines were measured using the fluorophosphonate probe fp-PEG-TAMRA using methods described previously (Liu et al., supra; Kidd et al., supra). Briefly, 40 µl of a 1 mg/ml solution of the soluble fractions of each cell lines were treated with 2 µM fp-PEG-TAMRA for one hour at ambient temperature. The labeling reactions were stopped by the addition of Laemmli buffer followed by boiling for 5 minutes. As a control for non-specific reaction of the probe, a duplicate sample was boiled for ten minutes prior to labeling with fp-PEG-TAMRA to denature all enzymatic activity. The labeled samples were resolved by 10% SDS-PAGE and visualized by scanning with a Hitachi flatbed scanner at 605 nm.

Alternatively, serine hydrolase activity in whole cells was measured with fp-Bodipy-Fl. Cells were plated in 24-well plates and the probe was added to a final concentration of 2 µM and labeled for one hour. The cells were lysed by the addition of Laemmli sample buffer followed by boiling. The labeled samples were resolved by 10% SDS-PAGE and visualized by scanning with a Hitachi flatbed scanner at 605 nm.

Inhibition of Serine Hydrolase Activity with Beta-Lactone Compounds.

Ebelactone A and B stocks were made in DMSO. Orlistat was made in EtOH. Cell lysate were generated at 1 mg/ml as described above. Samples (40 µg) were incubated with inhibitors for twenty minutes prior to addition of fp-PEG-TAMRA. The final concentration of DMSO or EtOH in each reaction was 10%. The labeling reactions were stopped by the addition of Laemmli sample buffer and samples were resolved on 10% SDS-PAGE and visualized.

Purification of Serine Hydrolases by Avidin-Biotin Affinity Chromatography.

Serine hydrolases were purified from 2.5 mg of soluble cell lysates by avidin-biotin affinity chromatography (Liu et al., supra; Kidd et al., supra). The lysates were pre-treated with avidin-agarose to remove non-specific binders. Lysates were labeled with fp-PEG-biotin (5 µM) for one hour at room temperature. Protein was separated from unincorporated fp-PEG-biotin by passage over a Nap 25 column. Protein containing fractions were pooled and SDS was added to a concentration of 0.5% and boiled for ten minutes. After boiling the samples were diluted with 50 mM Tris, pH 7.5 and 150 mM NaCl. Avidin-agarose was added to the solution for a one-hour incubation at room temperature. The agarose beads were pelleted by centrifugation and washed eight times with 50 mM Tris, ph 7.5, 150 mM NaCl and 1% Tween 20. Labeled protein was eluted by the addition of Laemmli buffer containing 1% SDS and boiling for ten minutes. Protein was resolved by 10% SDS-PAGE and detected by silver staining. Specific bands were extracted and subjected to in-gel trypsin digests and MALDI-TOF analysis as described previously (Landry et al. "A Method for Application of Samples to Matrix-Assisted Laser Desorption Ionization Time-of-Flight Targets That Enhances Peptide Detection." *Anal. Biochem.* 279:1-8, 2000; Harvey et al. "Insights into a plasma membrane signature." *Physiol. Genomics.* 5:129-136, 2001).

Detection of Fatty Acid Synthase by Western Blot.

MDA-MB-435 cells ($5 \times 10^4$) were seeded in 24 well plates. Following treatment with orlistat, cells were collected, suspended in Laemmli sample buffer and boiled. Protein was resolved by 10% SDS-PAGE and transferred to nitrocellulose. The membrane was blocked with non-fat milk and probed with an anti-FAS mAb (Pharmingen, San Diego, Calif.) followed by HRP-labeled rabbit anti-mouse IgG (Bio-Rad, Hercules, Calif.) and chemiluminescence detection with Western Lighting Chemiluminescence Reagent (Perkin-Elmer, Boston, Mass.).

Inhibition of Fatty Acid Synthesis by Orlistat.

Fatty acid synthesis in cells was measured by [$^{14}$C]-acetate incorporation (Kuhajda et al. "Fatty acid synthesis: a potential selective target for antineoplastic therapy." *Proc. Nat. Acad. Sci. U.S.A.* 91:6379-83, 1994; Pizer et al. "Pharmacological inhibitors of mammalian fatty acid synthase suppress DNA replication and induce apoptosis in tumor cell lines." *Cancer Res.* 58:4611-5, 1998). Cells were seeded at density of $2.5 \times 10^4$ cells/well in 24-well plates. Prior to the addition of orlistat, the wells were washed twice with PBS. Serum-free RPMI containing 300 µg/ml BSA and insulin/transferrin/selenium supplement was added to the wells, with or without orlistat. The cells were incubated for two hours prior to the addition of 1 µCi of [$^{14}$C]-acetate to label newly synthesized fatty acids. After two hours, the labeling medium was removed and the cells were washed with PBS/EDTA and trypsinized The cells pellets were washed twice more with PBS and fatty acids were extracted by the addition of an equal mixture of chloroform-methanol for 30 minutes. The extracted material was dried under a stream of $N_2$ gas and extracted further with water-saturated butanol. The butanol was removed by drying under a stream of $N_2$ gas and labeled fatty acids were detected by scintillation counting.

Detection of Orlistat-Induced Apoptosis.

Three breast cancer cell lines (MDA-MB-435, MDA-MB-231, and MCF-7) and human mammary epithelial cells (HMEC) were seeded in 96-well plates at $1 \times 10^4$ cells per well. The cells were washed twice with PBS and then incubated in serum free medium supplemented with 300 µg/ml BSA (Sigma) and insulin/transferrin/selenium cocktail (Life Technologies, Rockville, Md.) containing the indicated concentrations of orlistat. After twenty-four hours, the media was removed and the Cell Death Detection ELISA$^{plus}$ kit (Roche, Indianapolis, Ind.) was used to measure DNA fragmentation. The raw data were transformed to % cell death based on positive control standards.

Results

The Serine Hydrolase Profile of Mammary Carcinoma.

Figure 3:
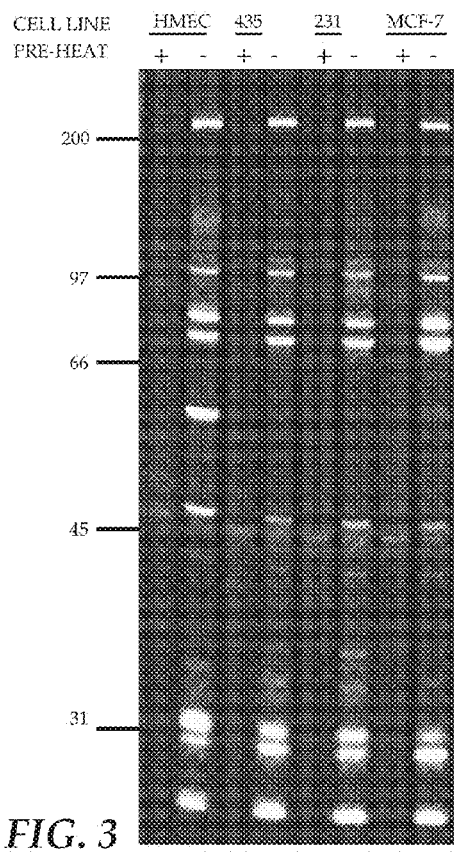
FIG. 3 shows a scan of an SDS-polyacrylamide gel that displays the serine hydrolase profile of normal and neoplastic mammary epithelial cells.

An activity-based probe was used to define the serine hydrolase profile of breast cancer cell lines. The probe is comprised of a fluorophosphonate warhead linked to the TAMRA fluorophore (FP-TAMRA) (Patricelli et al. "Direct visualization of serine hydrolase activities in complex proteomes using fluorescent active site-directed probes." *Proteomics* 1:1067-1071, 2001). Primary cultures of normal mammary epithelial cells (HMEC) were compared to three breast cancer cell lines, MCF-7, MDA-MB-231 and MDA-MB-435. These three lines represent a spectrum of phenotypes (Kurebayashi et al. "Quantitative demonstration of spontaneous metastasis of MCF-7 human breast cancer cells co-transfected with fibroblast growth factor 4 and LacZ." *Cancer Res.* 53:2178-2187, 1993; Shafie et al. "Formation of metastasis by human breast carcinoma cells (MCF-7) in nude mice." *Cancer Lett.* 11:81-87, 1980; and Price et al. "Tumorigenicity and metastasis of human breast carcinoma cell lines in nude mice." *Cancer Res.* 50:717-721, 1990). MCF-7 cells are estrogen responsive and non-invasive. The other two lines have lost estrogen control and are invasive in animals. Lysates from each cell type were reacted with FP-TAMRA and then resolved on SDS-PAGE (FIG. 3). In each case approximately fifteen different active hydrolases are visualized as fluorescent bands on SDS gels. The pattern of serine hydrolase expression is generally similar among the cell lines.

Screening for Serine Hydrolase Inhibitors.

We capitalized on the fact that FP-TAMRA reacts at the active site of all of the serine hydrolases visualized in FIG. 3, by performing a simultaneous screen for antagonists of all of these enzymes. Three beta-lactones were tested for the ability to block labeling of the mammary serine hydrolases by FP-TAMRA: ebelactones A and B, and orlistat.

Figure 4:
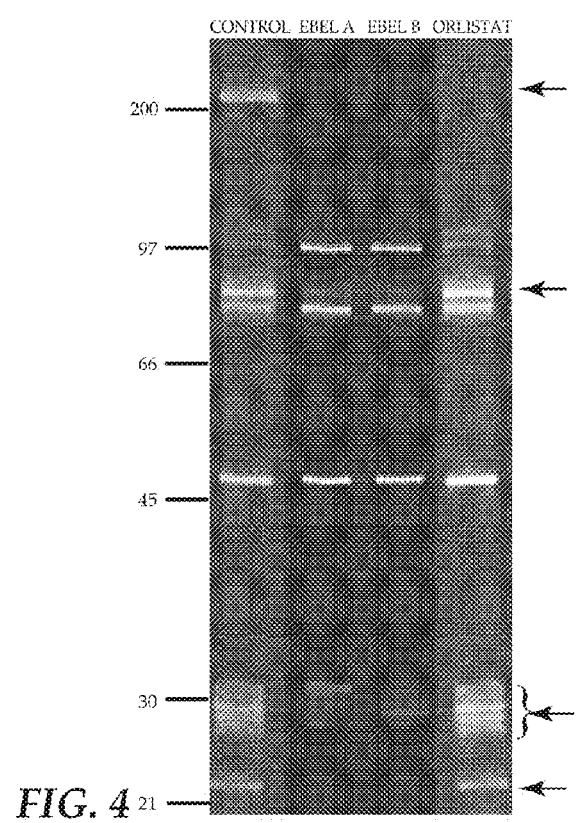
FIG. 4 shows a scan of an SDS-polyacrylamide gel from an experiment in which beta-lactones were screened for their ability to inhibit the activity of serine hydrolases.

Labeling of serine hydrolases in the cell lysates with FP-TAMRA was challenged with each of the beta-lactones Inhibition experiments were performed under pre-steady state conditions, so that relative $IC_{50}$ values could be compared. All three compounds blocked labeling of hydrolases by FP-TAMRA (FIG. 4), indicating inhibition at the active site serine. Interestingly though, each compound exhibited a different spectrum of inhibition. For example, ebelactone A was a potent inhibitor of the hydrolase expressed at 28 kDa, but ebelactone B had little effect on this enzyme. Conversely, ebelactone B abolished labeling of a hydrolase migrating at 31 kDa, but the same concentration of ebelactone A was far less effective. Tetrahydrolipstatin is selective for the hydrolase at 270 kDa that is expressed in breast cancer cell lines.

To identify the hydrolases that are inhibited by each beta-lactone, a slightly different labeling strategy was used. Cell lysates were reacted with a biotinylated derivative of fluorophosphonate (Liu et al., supra). Then, the tagged hydrolases were subjected to affinity purification on avidin-agarose columns Bands in the eluate corresponding to hydrolases hit by the beta-lactones were excised and subjected to peptide mass fingerprinting by MALDI-TOF mass spectrometry. In some instances the identification was confirmed by MS/MS sequencing. The 270 kDa band that is inhibited exclusively by orlistat was found to be fatty acid synthase (FAS). The identity of the protein was confirmed by immunoprecipitating the complex between FP-TAMRA and FAS with an anti-FAS monoclonal antibody.

Orlistat Inhibits FAS in Whole Cells and Blocks Cellular Fatty Acid Synthesis.

Studies were performed to determine whether orlistat could block the biological function of FAS in whole cells. MDA-MB-435 cells treated with a range of orlistat were probed with a membrane-permeable activity probe, FP-Bodipy. A concentration-dependent inhibition of the labeling of cellular FAS by orlistat was evident. These effects were independent of the abundance of FAS, which was measured from the same treated samples by Western blot. We measured the effects of orlistat on cellular fatty acid synthesis. MDA-MB-435 cells were fed [$^{14}$C]-acetate as a precursor, and treated with orlistat. At 100 μM orlistat the incorporation of [$^{14}$C]-acetate into cellular fatty acids was reduced by approximately 70%. This observation is taken to indicate that the biological activity of FAS in tumor cells is drastically reduced by orlistat.

Induction of Tumor Cell Apoptosis by Orlistat.

The effect of orlistat on apoptosis in the MDA-MB-435, MDA-MB-231 or MCF-7 mammary carcinoma cell lines, or in primary cultures of normal mammary epithelial cells or fibroblasts (HF cells; ATCC, Rockville, Md.), was measured using DNA fragmentation as an indicator. Cells ($1 \times 10^4$/well) were treated with orlistat in defined medium for 48 hours. Cells were lysed and DNA fragmentation was measured by ELISA and normalized to apoptosis induced by camptothecin. In each case triplicate measurements were made with a standard deviation of less then 10%.

Figure 5:
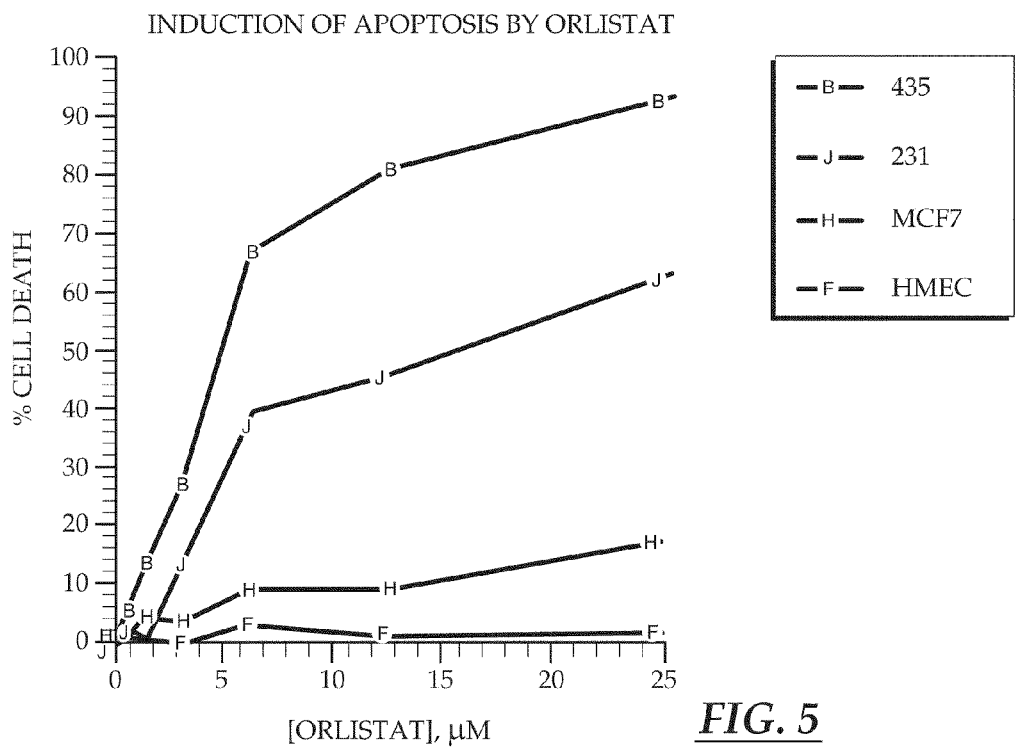
FIG. 5 is a graph showing the effect of orlistat on apoptosis of normal and neoplastic mammary epithelial cells.

Interestingly, orlistat induced an apoptotic response in all three tumor lines, without effect on normal HMECs (FIG. 5) nor on fibroblasts. The apoptotic response was most pronounced in the more differentiated tumor lines, MDA-MB-435 and MDA-MB-231. Orlistat had only a moderate effect on the MCF-7 cells. This analysis was extended by comparing the effect of orlistat on MDA-MB-435 cells and the HMECs across a range of orlistat. Half-maximal response in the MDA-MB-435 cells was observed at about 4 uM orlistat. No effect was evident in the HMECs.

Orlistat Induces $G_1/S$ Cell Cycle Arrest.

Figure 6:
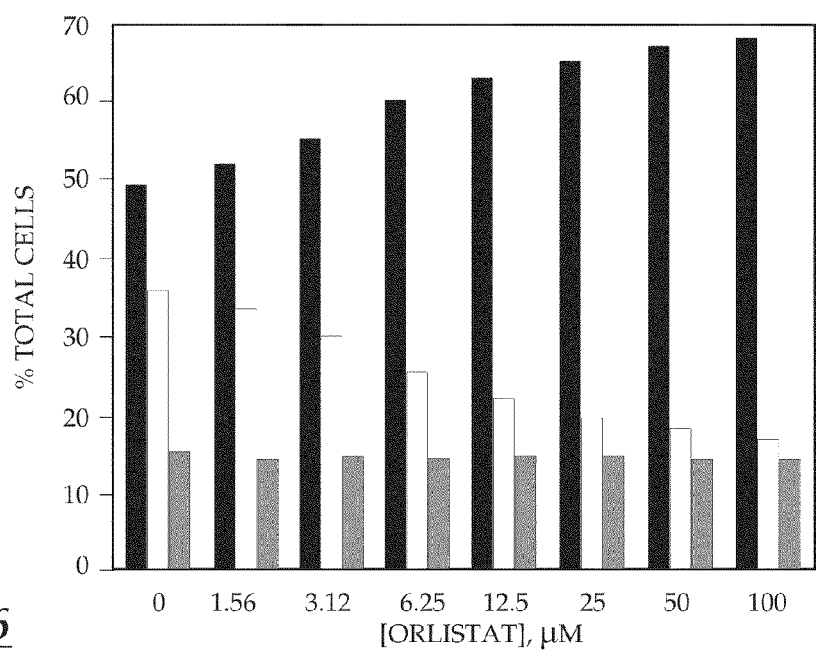
FIG. 6 is a graph showing the induction of cell cycle arrest in mammary carcinoma cells by orlistat.

To determine if the apoptotic effects of orlistat are associated with a cell cycle checkpoint, the effect of orlistat on cell cycle progression of the MDA-MB-435 cells was measured by staining cellular DNA with propidium iodide, and then assessing DNA content by flow cytometry. Treatment with orlistat caused a pronounced increase in the percentage of cells present in $G_1$, and a corresponding decrease in the percent of cells in S phase (FIG. 6: $G_1$=dark bars, S=open bars, and $G_2$/M=grey bars). These observations link the inhibition of FAS by orlistat to the Rb axis that controls $G_1/S$ progression.

Example III

Orlistat Inhibits Endothelial Cell Proliferation and FAS Activity

The experiments described below provide the first demonstration that human endothelial cells express FAS, and show that inhibition of FAS with orlistat induces a $G_1$ cell cycle block and inhibits endothelial proliferation.

Results

Orlistat Inhibits the Serine Hydrolase Activity of HUVEC Fatty Acid Synthase.

An activity-based probe, composed of a fluorophosphonate reactive group linked to the Tamra fluorophore (fp-TAMRA), was used to define the serine hydrolase profile of human umbilical vein endothelial cells (HUVEC). A cell lysate was allowed to react with fp-TAMRA and the proteins resolved by SDS-PAGE. Approximately 19 different hydrolases were detected as fluorescent bands on the gel. An intense band identified as fatty acid synthase (FAS) was evident close to the 220 kDa molecular weight marker.

Orlistat was assessed as an inhibitor of endothelial serine hydrolases by pre-incubating cell lysates with orlistat in a range of concentrations. FAS was the only hydrolase affected, showing a selective reduction in subsequent binding of fp-TAMRA. Orlistat inhibited FAS activity by a maximum of 80%, and orlistat concentrations of 5-10 uM were required to reach this level of inhibition. The half maximal effect was accomplished by 660 nM orlistat.

Orlistat Inhibits Proliferation of HUVECs.

The effect of orlistat on HUVEC proliferation induced by several mitogenic stimuli was assessed by BrdU incorporation. Orlistat and mitogen were added simultaneously to serum-starved cells, and BrdU included during the period equivalent to the second round of the cell cycle after mitogen addition. Orlistat inhibited proliferation induced by complete endothelial medium (containing a undefined mixture of mitogens), by bFGF and by VEGF. The minimal amount of proliferation occurring in basal medium supplemented with 0.2% fetal calf serum (FCS) only was also inhibited. Maximum inhibition was almost 90% for cells stimulated with complete medium or bFGF, but nearer to 80% when VEGF was used, and was achieved at orlistat concentrations of 10 uM and above. Orlistat concentrations required for a half maximal effect were 4 uM, 1 uM and 1.25 uM respectively.

Orlistat Induces G1 Cell Cycle Arrest.

Progression of HUVEC through the cell cycle was monitored by flow cytometric assessment of DNA content. After 24 h serum starvation, few cells were undergoing cell division; the distribution of cells between G1, S and G2/M phases was 67%, 6% and 27%, respectively. In the absence of orlistat, cells re-exposed to Endothelial Growth Medium entered S phase 12 h later, with DNA synthesis reaching a population maximum at 16 h. The percentage of cells in G2/M peaked 4 h later, at 20 h, after which the cells rapidly re-entered S phase. In the presence of 10 uM orlistat, entry into the first round of S phase was partially blocked, with a corresponding increase in the percentage of cells remaining in G1, and decrease in cells progressing on to G2/M phase. The second S phase peak was completely inhibited by orlistat, with the cells remaining in G1. These observations indicate that orlistat induces a G1 cell cycle block in HUVECs.

Methods

Effect of Orlistat on FAS Activity in HUVEC Lysates.

HUVEC lysates (40 ug) were preincubated for 30 min with orlistat at concentrations ranging from 10-0 uM, followed by a one hour incubation with fp-TAMRA to tag any remaining active sites. Non-specific labeling with the probe was determined by boiling samples prior to the addition of fp-Tamra.

Reactions were stopped by addition of SDS loading buffer, followed by boiling. Proteins (30 ug/lane) were resolved by SDS-PAGE using a 10% gel, and visualized at 605 nm using a Hitachi flat bed gel scanner. The density of the band corresponding to FAS was measured using Image Analysis v2.0 software (Hitachi Genetic Systems) and the effect of orlistat on FAS activity was expressed as a percentage of the band intensity in the untreated lysate.

Effect of Orlistat on Endothelial Cell Proliferation.

Cell proliferation was measured by incorporation of BrdU. HUVEC were seeded in 96 well plates at a density of 2000 cells/well and cultured in Endothelial Growth medium (EGM; Clonetics, Walkerville, Md.) for 24 h at 37° C. Cells were serum-starved for further 24 h in Endothelial Basal Medium (EBM; Clonetics, Walkerville, Md.)+0.2% FCS. Medium was replaced with orlistat (40-0 uM) diluted in (A) EGM, (B) EBM+2% FCS+bFGF (5 ng/ml), (C) EBM+2% FCS+VEGF (20 ng/ml) or (D) EBM+0.2% FCS. Cells were incubated 48 h at 37 deg C., with BrdU present during the final 24 h. Medium was removed, the cell monolayers fixed, and BrdU incorporation measured by ELISA. Proliferation was expressed as a percentage of that measured in the absence of orlistat.

Effect of Orlistat on HUVEC Passage Through the Cell Cycle.

HUVEC were seeded into 6-well plates at a density of 74,000 cells/well and cultured in EGM for 24 h at 37 deg C. Cells were serum-starved for further 24 h in EBM+0.2% FCS. Medium was replaced with EGM+/−10 uM orlistat, and cells cultured for up to 38 h more. Untreated and orlistat-treated cells were sampled at 4 h intervals. The DNA content of cells was assessed by binding of propidium iodide, and percentage of cells in (A) G1 phase, (B) S phase and (C) G2/M phase at each time point was calculated.

Example IV

Sequential In Situ Ketene Generation, Dimerization and Hydrogenation for the Catalytic, Asymmetric Synthesis of β-Lactones The current discovery that beta-lactones inhibit serine hydrolase activity prompted development of the following novel process for synthesizing optically active beta-lactones from achiral starting material.

Results

The development of a concise, asymmetric route to psuedosymmetric 3,4-dialkyl-cis-beta-lactones, analogous to the FDA approved anti-obesity agent tetrahydrolipstatin is reported in this example. The process is based a two-step process of ketene dimerization/hydrogenation from acid chlorides, followed by subsequent alpha-epimerization and alpha-alkylation or acylation leading to beta-lactones bearing quaternary carbons. These beta-lactones displayed antagonistic activity (apparent Ki's in the .micro.M range) in competition with a fluorogenic substrate toward a recombinant form of the thioesterase domain of fatty acid synthase, which has great potential as a new therapeutic target for cancer.

A Novel Two-Step Synthesis Method for Obtaining Asymmetric Beta-Lactones from Acid Chloride.

According to the present invention there is provided a process of preparing achiral beta-lactones comprising the steps of: forming a ketene dimer from an acid chloride and hydrogenating the ketene dimer to generate a cis-beta-lactone. The invention process is generally represented by Scheme I

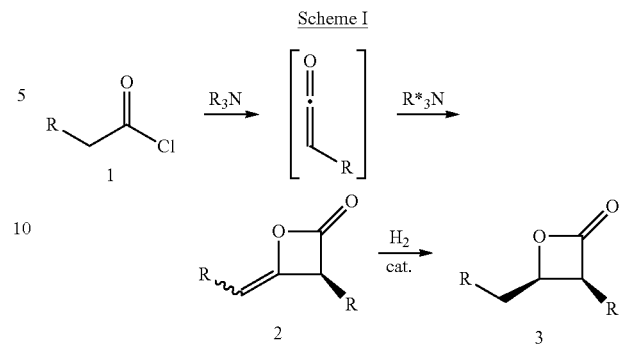

Scheme I

Step 1: Formation and Isolation of Ketene Dimers.

In forming a ketene dimer by the current method, an acid chloride having the formula VI is used as a starting material. The acid chloride has the formula VI:

VI wherein R can be a hydrogen, an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group.

Previous large scale synthesis and purification of racemic ketene dimers bearing long alkyl chains (>13 carbons) relied on acidic extraction to remove alkyl ammoniums salts followed by vacuum distillation. Because many functionalities are acid sensitive, the current synthesis method preferably utilizes silica gel chromatography. Ketene dimers were purified by silica gel flash chromatography although the yields were decreased relative to direct transformation. The yield of ketene dimer was improved slightly by use of doubly distilled acid chloride (78% vs 62% yield, Table 1, entry 5).

TABLE 1

| entry | catalyst | time (h) | % yield[a] | % ee[c] |
|---|---|---|---|---|
| 1 | QND (9) | 24 | 58 | 98 |
| 2 | O-TBS QND (10) | 24 | 54 | ND |
| 3 | O-TMS QND (10) | 24 | 55 | ND |

TABLE 1-continued

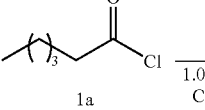

| entry | catalyst | time (h) | % yield[a] | % ee[c] |
|---|---|---|---|---|
| 4 | O-TMS QUIN (12) | 6 | 62 | ND |
| 5 | O-TMS QUIN (12) | 6 | 78[b] | 96 |

[a]Yields refer to isolated, purified dimer.
[b]Freshly, doubly distilled acid chloride was used.
[c]ND not determined.
QND means_quinidine;
O-TBS QND means O-t-butyl dimethyl silyl quinidine;
O-TMS QND means_O-trimethylsilyl quinidine;
O-TMS QUIN means O-trimethylsilyl quinine.

One ketene dimer, referred to as 3a in Table 2 below, possessed sufficient stability to determine its enantiomeric purity by gas chromatography using cyclodextrin bis-OTBS as chiral stationary phase. Both enantiomers of ketene dimer 3a were obtained in high optical purity using either QND (>98% ee) or O-TMS QUIN (>96% ee). The enantiopurity of other dimers were determined following hydrogenation to the cis-beta-lactones (vide infra). We found that silylated alkaloids were superior catalysts in terms of reaction efficiency for the ketene dimerization step as compared to acetylated derivatives (formed in situ) as has been previously reported by Calter. (See, M. A. Calter, J. Org. Chem. 1996, 61, 8006; M. A. Calter, R. K. Orr, W. Song, Org. Lett. 2003, 5, 4745; and R. K. Orr, M. A. Calter Tetrahedron 2003, 59, 3545.)

Step 2: Hydrogenation of Ketene Dimers.

Prior hydrogenation studies of diketenes have primarily focused on the parent diketene, 4-methylene-2-oxetanone, in both racemic and asymmetric fashion, as a means to obtain the corresponding 3,4-dimethyl-2-oxetanone, which is a commodity chemical utilized on ton scale for polymer applications. Several catalysts have been utilized for hydrogenation of enol ethers, however for simplicity and practicality palladium on carbon is initially used in this example with racemic ketene dimer 2a (entry 1, Table 2).

At the outset, we expected high facial selectivity for the hydrogenation due to the proximity of the alkene to the alpha-stereogenic carbon at C3 of the beta-lactone. A high degree of diastereoselectivity was observed during epoxidations of many of these ketene dimers. However, hydrogenation of dimer 2a employing 5 mol % Pd/C (5 wt %) resulted in high yield but low diastereoselectivity providing a mixture of cis- and trans-beta-lactones 3a (4:1 favoring cis) after a 24 h reaction time (entry 1, Table 2). To reduce the activity of the catalyst, 100 mol % triethylamine relative to Pd catalyst was added. The addition of triethylamine also improved the diasteroselectivity to 17:1 with the same reaction time (entry 2, Table 3). However, repeating these conditions with optically active dimer 2a (98% ee) indicated that racemization was occurring under these conditions necessarily at the dimer stage providing cis-beta-lactone 3a with reduced enantiopurity (71% ee). Shortening the reaction time using 5 mol % catalyst without added $Et_3N$ also gave high diastereoselectivity. Taken together, these results suggest that either long reaction times or the absence of catalyst poison leads to erosion in diastereoselectivity. Optimal conditions that prevented racemization, maintained high diastereoselectivity, and reduced reaction time were eventually realized by decreasing the amount of Pd/C to 1 mol % and reducing the reaction time to 30 min under 30 psi of $H_2$ pressure. Under these conditions, no racemization or epimerization was observed for either of the ketene dimer or major diastereomer isolated, cis-beta-lactone 3a. The latter could be isolated in 90% yield and 96% ee and >19:1 diastereomeric ratio (Table 3, entry 4) as determined by coupling constant analysis (JHa,Hb=6.3 Hz).

TABLE 2

Catalytic asymmetric beta-lactone synthesis via a sequential, two-step ketene dimerization/hydrogenation sequence.

| entry | R | ketene dimer (2) | % yield (2)[b] | beta-lactone (3) | % yield (3)[c] | % ee (3)[d] |
|---|---|---|---|---|---|---|
| 1 | n-butyl | 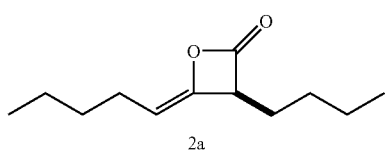 2a | 75 | 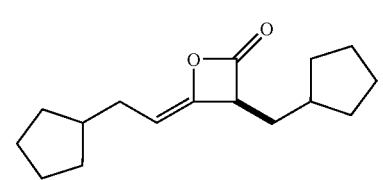 3a | 90 | 96 |
| 2 | cyclopentyl | 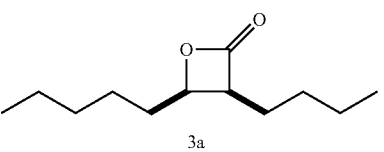 2b | 54 | 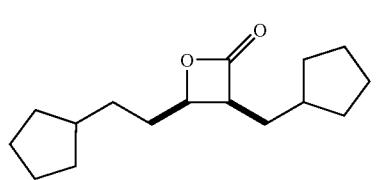 3b | 89 | 94 |

TABLE 2-continued

Catalytic asymmetric beta-lactone synthesis via a sequential, two-step ketene dimerization/hydrogenation sequence.

| entry | R | ketene dimer (2) | % yield (2)[b] | beta-lactone (3) | % yield (3)[c] | % ee (3)[d] |
|---|---|---|---|---|---|---|
| 3 | cyclohexyl | 2c | 55 | 3c | 89 | 90 |
| 4 | benzyl | 2d | 48 | 3d | 85 | 96 |
| 5 | CH$_2$CO$_2$Me | 2e | 60[e] | 3e | 94 | 92 |
| 6 | 11-methoxynonyl | 2f | 62[f] | 3f | 94 | ND |

[a]All reactions were carried out at 0.1 M (final concentration) with freshly distilled acid chloride.
[b]Refers to isolated, purified yields.
[c]Enantiomeric excess was determined by chiral GC analysis.
[d]Absolute configuration of the major enantiomer is depicted.
[e]Reaction time was 3 h at 0° C.
[f]Reaction time was 3.5 h with 5 mol % catalyst 7.

TABLE 3

Effect of catalyst loading, base, and reaction time on diastereoselectivity and enantioselectivity.[a]

| entry | mol % Pd/C | mol % Et$_3$N | time (h) | % yield | dr[b] |
|---|---|---|---|---|---|
| 1 | 5 | 0 | 24 | 88 | 4/1 |
| 2 | 5 | 100 | 24 | 92 | 17/1 |
| 3 | 5 | 0 | 0.5 | 89 | 17:1 |
| 4 | 1 | 0 | 0.5 | 90 | >19:1[c] |

[a]Reactions were conducted at 0.1 M in CH2Cl2.
[b]Ratios estimated by 1H NMR (500 MHz) integration of Ha and Hb in crude reaction mixtures.
[c]Enantiomeric excess determined by GC analysis to be 98% ee.

Figure 7:
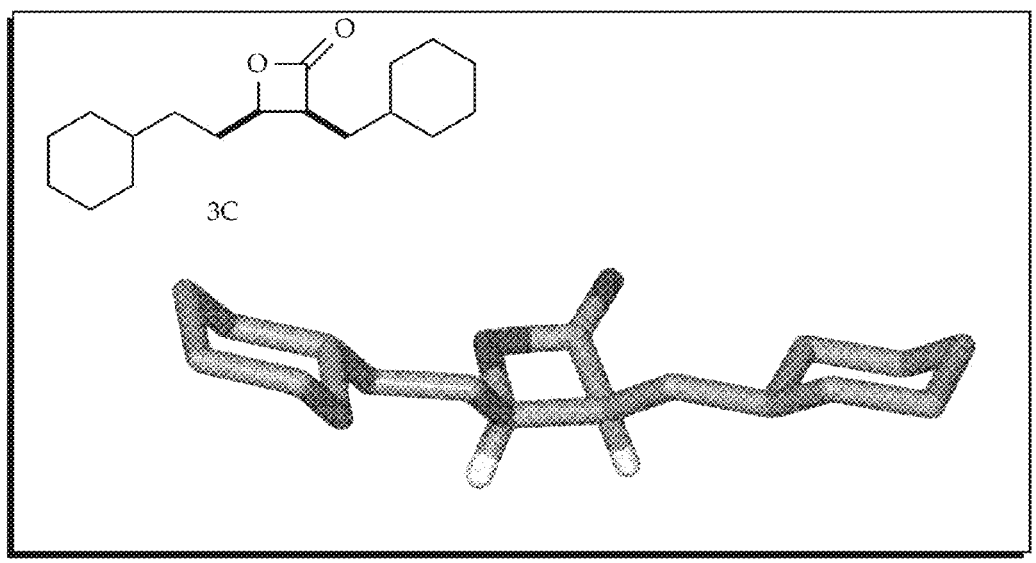
FIG. 7 is an X-ray crystal structure (POV Chem rendering) of beta-lactone 3c.

In this example it is shown that the hydrogenation of a series of ketene dimers 2a-f (Table 2) results in consistently high yields of the corresponding beta-lactones 3a-f (Table 2) with high enantiomeric purities (Table 3). Enantiomer ratios were determined by chiral GC analysis following hydrogenation. Beta-Lactone 3c was crystalline and thus x-ray analysis verified the cis stereochemistry obtained during hydrogenation (FIG. 7). Compounds that have been synthesized by this method are shown in FIGS. 10, 11 and 12.

One-Pot Ketene Dimerization Sequence.

Figure 8:
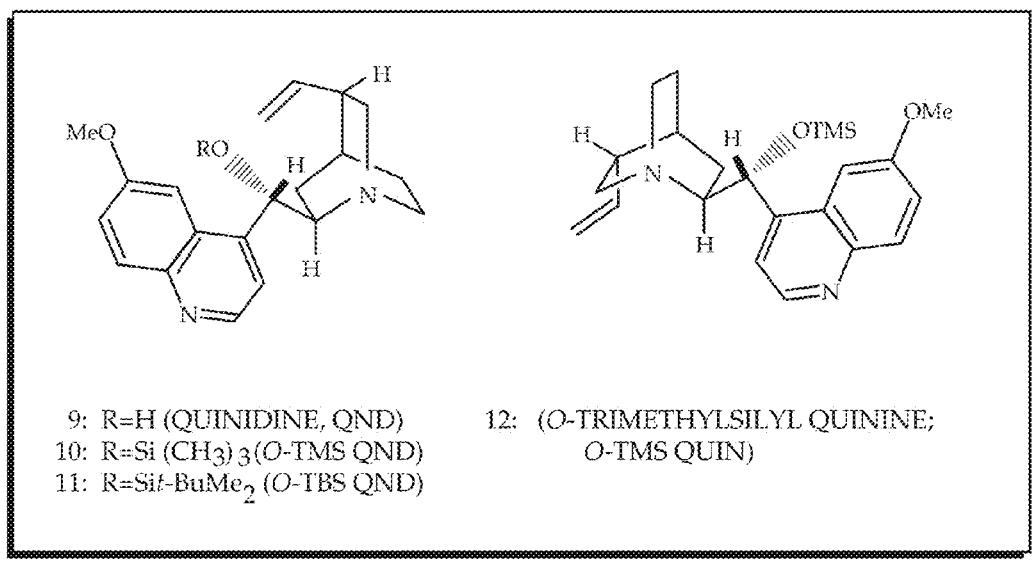
FIG. 8 illustrates some of the cinchona alkaloids and derivatives 9-11 employed in the ketene dimerization.

In an alternative embodiment of the novel two-step synthesis method, the reaction is carried out as a one-pot, two step ketene dimerization/hydrogenation process. (Scheme IV). In the example the reaction employs hexanoyl chloride to access the corresponding beta-lactone. (entry 1, Table 2) Following ketene dimerization by the method of Calter employing quinidine (FIG. 8) and simple filtration to remove amine hydrochloride salts, the reaction was transferred to a hydrogenation vessel and pressurized to 30 psi of H.sub.2. This procedure provided only modest yields of beta-lactone 3a in this manner due to presumed degradation of the ketene dimers in the presence of traces of dissolved quaternary ammonium salts, a process with precedent in the literature.

Scheme IV

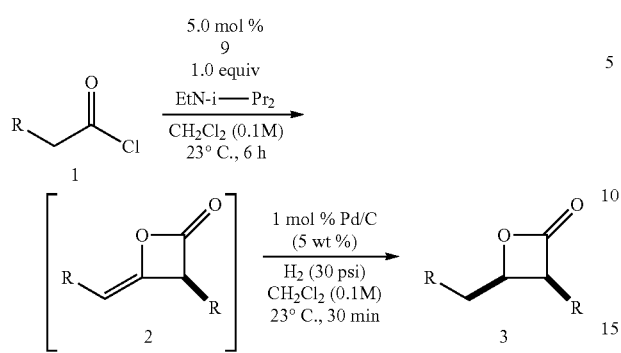

Despite careful filtration of the amine salts prior to hydrogenation, extensive degradation of the dimer was observed. More importantly, the enantiomeric purity of the ketene dimer was found to erode during the hydrogenation, (97% to 78% ee at 40% conversion) and thus the purity of the beta-lactone (97% to 74% ee). This method, therefore, is less desirable than the preferred embodiment for obtaining the desired optically enriched beta-lactones. The stereochemistry of beta-lactone 3a was assigned based on coupling constant analysis (Jcis ~6 Hz, Jtrans 4-4.5 Hz) and subsequently confirmed by x-ray analysis of beta-lactone 3c (FIG. 7).

Reaction Analysis by Reaction View Spectroscopy.

Figure 9A:
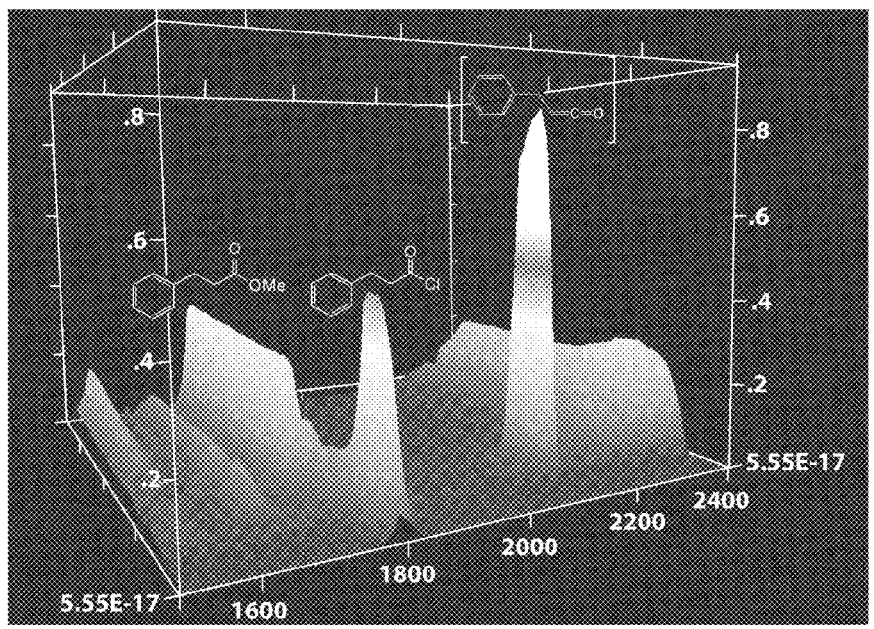
FIG. 9a and FIG. 9b is a three-dimensional plot illustrating in situ IR spectroscopy (Reaction View) monitoring of: (a) ketene formation from hydrocinnamyl chloride at 23 .deg.C. followed by addition of methanol leading to methyl cinnamate; (b) the ketene dimerization of hydrocinnamyl chloride mediated by quinuclidine hydrochloride (5 mol %) and EtNi—Pr2 (1.0 equiv).
Figure 9B:
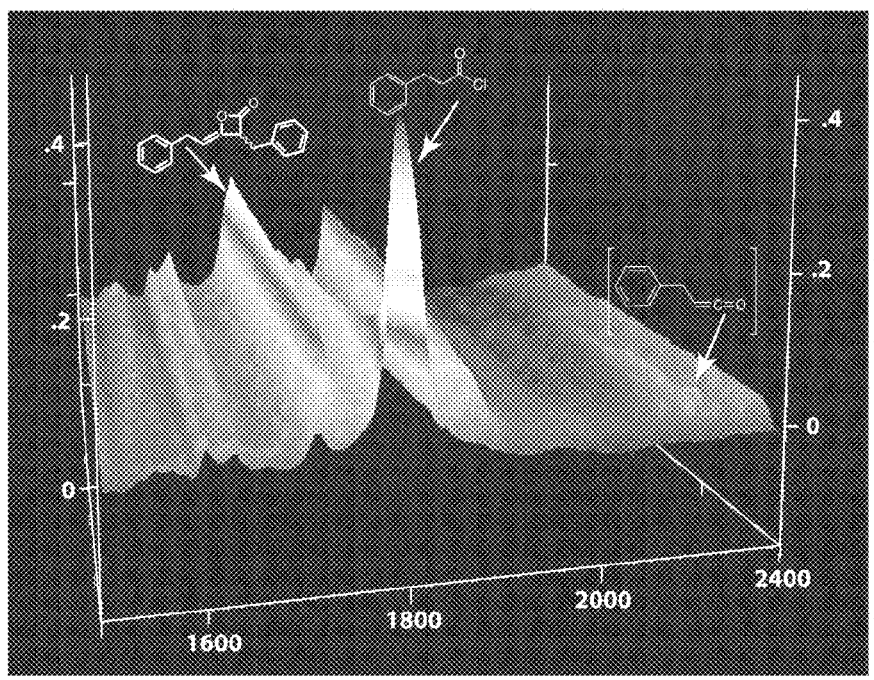

The dimerization and related processes were monitored by in situ IR (ReactionView, Scientific Optical Solutions Ltd, Cathcart, Glasgow, Scotland) spectroscopy. The formation of ketene from hydrocinnamoyl chloride (entry 4, Table 2) followed by addition of MeOH to form the corresponding methyl ester was analyzed first. Interestingly, generation of ketene appears complete within a short time and persists until MeOH is added leading to a fast conversion to methyl cinnamate. A dimerization process leading to the phenyl bearing ketene dimer 3d was studied at 23. deg.C. using quinuclidine hydrochloride .as nucleophilic catalyst and Hunig's base as stoichiometric. Base (FIGS. 9a and 9b). Addition of hydrocinnamyl chloride (1793 cm$^{-1}$) leads to a brief appearance of ketene (2118 cm$^{-1}$) with concomitant formation of ketene dimer 2d (1710 cm−1). The disappearance of ketene and acid chloride prior to complete formation of ketene dimer is suggestive of a very fast dimerization step or generation of another intermediate that is short-lived. Indeed, dimerization is complete within 1 hour, as shown.

Beta-Lactones that are Structurally Similar to Orlistat can be Obtained from Acid Chlorides in Three Steps.

The two-step synthesis method described directly above can subsequently include the steps of, epimerizing the cis-beta-lactone to produce the trans-beta-lactone in a mix, or alkylating or acylating the cis-beta-lactone to form trisubstituted-beta-lactones. These subsequent processes are generally presented in Scheme II and Scheme III, respectively.

Scheme II

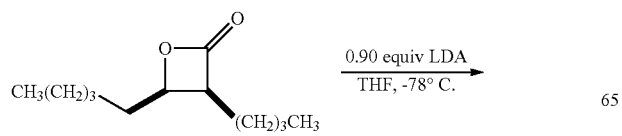

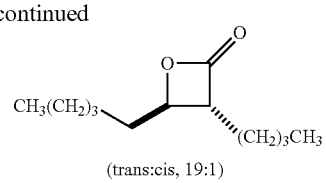

(trans:cis, 19:1)

Scheme III

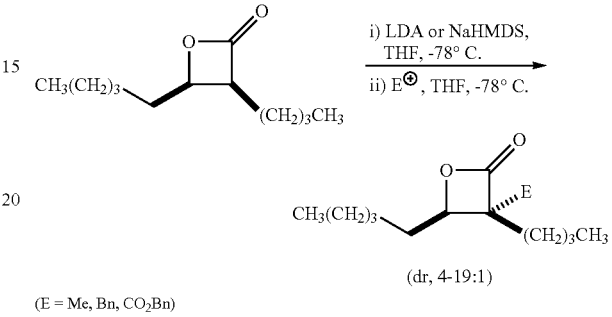

(E = Me, Bn, CO$_2$Bn)

Epimerization of Cis-Beta-Lactones.

As described above, the majority of naturally-occurring beta-lactones possess trans-beta-lactone stereochemistry including Orlistat. Thus, this example describes conditions to epimerize to the thermodynamically preferred trans-beta-lactones. Interestingly, deprotonation leading to beta-lactone enolates is possible since beta-elimination in these systems is a symmetry forbidden process. Competing Claisen condensation can be precluded provided there is an alpha-substituent. Several thermodynamic conditions to effect epimerization were studied and the most promising was that using a triethylamine/ammonium acetate buffer system in dichloromethane. However, use of this buffer system only led to from 10 to 15% up to ~40% conversion diastereomeric ratio (dr) by $^1$H NMR analysis after prolonged stirring at 23. deg.C. After some investigation, we found that deprotonation with lithium hexamethyldisilazide under kinetic conditions followed by low temperature quenching with acetic acid provided a mixture of cis- and trans-isomers in moderate yield which could be separated by chromatography (Scheme V).

Specific examples of epimerized beta-lactone compounds that have been synthesized by this process are shown in FIG. 11. Moreover, synthesized beta-lactones closely resembling tetrahydrolipstatin and pancilicin D are shown in FIG. 12.

Scheme V

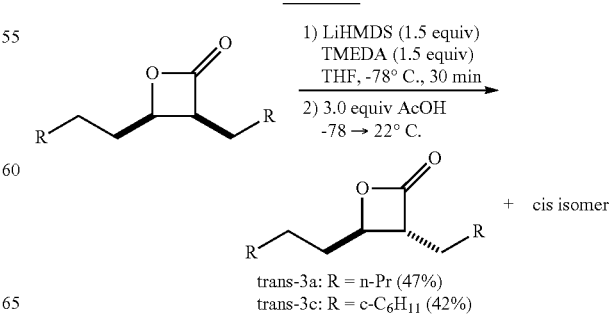

trans-3a: R = n-Pr (47%)
trans-3c: R = c-C$_6$H$_{11}$ (42%)

Alkylation/Acylation of Cis-Beta-Lactones to Form Trisubstituted Beta-Lactones.

Cis-beta-lactone structures synthesized using the novel synthesis method of the current invention can be further modified to produce diastereomer compounds.

For example, enolization with LDA followed by addition of various electrophiles allowed access to beta-lactones bearing alpha-quaternary carbons. These reactions proceeded with high diastereoselectivities for bulky alkylating and acylating agents whereas smaller electrophiles such as methyl iodide provided moderate diastereoselectivity (entry 1, Table 4; dr, 4:1). Use of LiHMDS and NaHMDS led to similar yields and selectivities in the case of beta-lactones 8b and 8c, respectively. Compounds that have been synthesized by this method are shown in FIGS. 11 and 12.

TABLE 4

Diastereoselective alkylations and acylations of cis-beta-lactone 4a leading to quaternary carbon bearing beta-lactones 8a-c.

| entry | R | cmpd. no. | base | % yield$^a$ | dr$^b$ |
|-------|---|-----------|------|------------|--------|
| 1 | CH$_3$ | 8a | LDA | 80 | 4:1 |
| 2 | Benzyl | 8b | LiHMDS | 61 | 19:1 |
| 3 | CO$_2$Benzyl | 8c | NaHMDS | 74 | 19:1 |

$^a$Refers to isolated, purified yield.
$^b$Diastereomeric ratio was determined by integration (1H NMR 500 MHz).

Methods

General Experimental Procedure for Dimerization as Described for (R,Z)-3-butyl-4-pentylideneoxetan-2-one (2a). To a flame dried 1 L round bottom flask was added 764 mg (5 mol %, 1.926 mmol) TMS-quinine, 385 mL CH$_2$Cl$_2$ (0.1M) and 6.86 mL (1.0 equiv, 38.53 mmol) of Hunig's base under nitrogen atmosphere at 22° C. To this colorless solution, 5 mL (5.18 g, 38.53 mmol) of freshly double-distilled, hexanoyl chloride was added over 15 min via syringe. After 6 h the dark yellow solution was concentrated down to 100 mL (⅕ original volume) in vacuo and 250 mL of pentanes was added to precipitate the ammonium salts. Filtration through Whatmann filter paper (#1, qualitative grade), concentration in vacuo and purification by flash column chromatography on deactivated SiO$_2$ (10% H$_2$O) (2.5 cm×35.0 cm column, 15 cm pad) eluting with 0→20% Et$_2$O: hexanes gave 2.83 g (75%) of 2a as a colorless oil (96% ee, chiral GC analysis). R$_f$ 0.54 (15% Et$_2$O:hexanes); IR (thin film) 1865 cm$^{-1}$; $^1$H NMR (300 MHz, CDCl$_3$) δ 4.70 (dt, J=6.3, 1.3 Hz, 1H), 3.94 (dt, J=1.0, 7.0 Hz, 1H), 2.13 (app q, 2H), 1.75-1.83 (m, 2H), 1.28-1.53 (m, 8H), 0.88-0.96 (m, 6H); $^{13}$C NMR (300 MHz, CDCl$_3$) δ 14.5, 14.6, 22.9, 23.1, 25.1, 28.0, 29.2, 32.3, 54.45, 102.4, 146.4, 170.6; ESI LRMS Calcd. For C$_{12}$H$_{20}$O$_2$[M+Li]: 202. Found: 202.

Racemic ketene dimers were initially prepared in a similar manner using Hünig's base. Subsequently, 5 mol % quinuclidine hydrochloride with 1.0 equiv of Hunig's base gave optimal results (reaction rate and yield) therefore this method was used for preparation of racemic ketene dimers.

Representative Procedure for Hydrogenation as Described for (3R,4S)-3-butyl-4-pentyloxetan-2-one (3a).

The purified n-butyl ketene dimer 2a, (5.1 mmol, 1.0 g) was dissolved in 40 mL dichloromethane (0.1 M) and transferred to a Parr bomb apparatus under a N.sub.2 atmosphere using an additional 10 mL dichloromethane as wash solvent. Pd/C (107 mg, 1 mol %, 5 wt %) was then added at one time under N.sub.2 atmosphere. The Parr bomb was then subjected to three consecutive evacuation-saturation cycles of hydrogen gas and then pressurized to 30 psi hydrogen gas pressure. Hydrogenation with shaking (Parr shaker) was continued for 30 min at this pressure and then the heterogeneous slurry was vacuum filtered through a plug of Celite, and concentrated yielding a colorless oil. Flash chromatography with gradient elution (5→15% diethyl ether/hexanes; 2.5×35.0×5 cm pad) gave 3-butyl-4-pentyl-oxetan-2-one (3a, 897 mg, 90%) as a colorless oil (>96% ee, chiral GC): Rf 0.47 (15% Et2O: hexanes); IR (thin film) 1824 cm-1; 1H NMR (300 MHz, CDCl.sub.3) δ 4.54 (ddd, J=2.1, 3.6, 5.7 Hz, 1H), 3.59 (ddd, J=4.5, 5.4, 8.4 Hz, 1H), 1.46-1.84 (m, 6H), 1.31-1.44 (m, 8H), 0.88-0.94 (m, 6H); $^{13}$C NMR (500 MHz, CDCl$_3$) δ 173.1, 76.5, 53.3, 32.2, 30.9, 30.5, 26.0, 24.4, 23.2, 23.2, 14.7, 14.5; ESI LRMS Calcd. for C12H22O2 [M+Li]: 205. Found: 205.

The enantiomeric purity of ketene dimer 2a and β-lactone 3a was determined to be >96% e.e by chiral GC analysis. Column Type: chiral bis-OTBS-cyclodextrin; retention time: tdimer 16.96 (major), tdimer 17.16 (minor); tβ-lactone 26.23 (major), tβ-lactone 26.44 (minor). Conditions: make up flow: 25 mL/min; H2 flow: 30 mL/min; air flow: 300 mL/min; injector: temperature: 200° C., pressure: 5 psi (hold time: 30 min); oven: temperature gradient: 100→140° C. (hold time: 30 min); detector temperature: 250° C.

(3R,4R)-3-butyl-4-pentyloxetan-2-one (3a)

To a −78° C. solution of 100 mg (0.51 mmol) of 3a in 5 mL THF was added 760 μL LiHMDS (1.5 equiv, 1.0 M in THF) and allowed to stir for 1 h. Tetramethylenediamine (TMEDA, 120 μL, 1.5 equiv, 0.76 mmol) was then added at −78° C. and allowed to stir for an additional 30 min after which the solution was quenched with glacial acetic acid (130 μL, 3.0 18 equiv, 2.27 mmol) and the mixture was warmed to 22° C. After extraction with diethyl ether (2×6 mL), the combined organics were washed with 2 mL pH 7.0 buffer and 2 mL brine and then dried over Na2SO4. Concentration in vacuo gave a colorless oil which upon purification by flash chromatography on SiO$_2$ (15% Et2O: hexanes) gave cis-3a and trans-3a (72 mg, 72% yield) as a 1:1 mixture of diastereomers. Further purification by gravity column chromatography (5% Et2O:hexanes) delivered 34 mg of trans-3a: Rf 0.38 (10% Et2O:hexanes; cis-3a: Rf 0.29); IR (thin film) 1824 cm−1; 1H NMR (500 MHz, CDCl$_3$) δ 4.22 (ddd, J=4.2, 6.0, 7.5 Hz, 1H), 3.16 (ddd, J=3.9, 6.6, 9.0 Hz, 1H), 1.67-1.93 (m, 4H), 1.26-1.49 (m, 10H), 0.91 (bs, 6H); $^{13}$C NMR (300 MHz, CDCl$_3$): 14.5, 14.7, 23.1, 23.2, 25.4, 28.3, 29.9, 32.1, 35.2, 56.9, 78.9, 172.5; ESI LRMS Calcd for C12H22O2 [M+Li]: 205. Found: 205.

(3R,4S)-3-butyl-3-methyl-4-pentyloxetan-2-one (8a)

A solution of β-lactone 3a (36.3 mg, 0.1835 mmol) in 1.9 mL THF was cooled to −78° C. and 370 μL of LiHMDS (0.367 mmol, 2.0 equiv, 1.0 M solution in THF) was added under a nitrogen atmosphere. After 1.5 h, 23 μL (0.367 mmol, 2.0 equiv) of iodomethane was added and the reaction warmed to −40° C. and stirred for an additional 45 min. The reaction mixture was concentrated in vacuo and purified by flash chromatography (0→15% Et2O:hexanes) to give β-lactone 8a (28.4 mg, 73%) as a colorless oil and as a mixture of cis/trans diastereomers (dr, 6:1). Data provided for major diastereomer: Rf (15% Et2O:hexanes) 0.64; IR (thin film) 1824 cm−1; 1H NMR (500 MHz, CDCl$_3$) δ 4.18 (dd (major diast.), J=6.0, 8.5 Hz, 1H), 1.63-1.78 (m, 2H), 1.45-1.53 (m, 2H), 1.39 (s, 3H), 1.24-1.39 (m, 10H), 0.89-0.94 (m, 6H); $^{13}$C NMR (500 MHz, CDCl$_3$) 14.1, 14.2, 20.0, 22.1, 25.5, 25.6, 26.5, 30.3, 31.7, 35.9, 56.8, 84.5, 175.5; ESI LRMS Calcd. for C13H24O2Li [M+Li]: 219. Found: 219.

(3S,4S)-3-benzyl-3-butyl-4-pentyloxetan-2-one

To a −78° C. solution of β-lactone 3a (153 mg, 0.76 mmol) dissolved in 7.5 mL THF was added 1.52 mL LiHMDS (1.52 mmol, 2.0 equiv, 1.0 M solution in THF) under nitrogen atmosphere. After 1.5 h, 180 μL (1.52 mmol, 2.0 equiv) of benzyl bromide was added and the reaction warmed to −40° C. and stirred for an additional 45 min. The reaction mixture was concentrated in vacuo and purified by flash chromatography (0→5% Et2O:hexanes) to give β-lactone 8b (192 mg, 88%) as a mixture of cis/trans diastereomers (>19:1). Data provided for major diastereomer: Rf 0.55 (5% Et2O:Hexanes); IR (thin film) 1813 cm−1; 1H NMR (500 MHz, CDCl$_3$) δ 7.30-7.34 (m, 2H), 7.25-7.28 (m, 1H), 7.16-7.17 (m, 2H), 4.34 (dd, J=4.5, 9.5 Hz, 1H), 3.13, 2.88 (AB q, J=14.5 Hz, 2H), 1.68-1.78 (m, 2H), 1.45-1.61 (m, 4H), 1.18-1.39 (m, 8H), 0.94 (t, J=3.5, 3H), 0.87 (t, J=3.5, 3H); 13C NMR (500 MHz, CDCl$_3$): 13.87, 13.89, 22.4, 23.2, 25.2, 26.3, 28.7, 29.7, 31.4, 38.2, 61.3, 80.3, 127.1 (2C), 128.7 (2C), 129.8, 135.8, 174.2; ESI LRMS Calcd. for C19H28O2 [M+Li]: 295. Found: 295.

(3S,4S)-benzyl 3-butyl-2-oxo-4-pentyloxetane-3-carboxylate (8c)

To a −78° C. solution of NaHMDS (1.2 equiv, 0.91 mmol, 45 μL, 2M in THF) in 5 mL THF was added 150 mg (0.73 mmol) of β-lactone 3a dissolved in 2.5 mL THF. After 1.5 h, benzylchloroformate (1.1 equiv, 0.833 mmol, 120 μL) was added at one time and stirred for an additional 3 h. This solution was warmed to 23° C. over 1 h and worked up as described above for β-lactone 8b. Flash chromatography on SiO2 (5% Et2O:hexanes) gave β-lactone 8c (185 mg, 74% yield) as a colorless oil: Rf 0.48 (15% Et2O:Hexanes); IR (thin film) 1824, 1757, 1716 cm−1; 1H NMR (300 MHz, CDCl$_3$) δ 7.40 (m, 5H), 5.27, 5.22 (AB q, J=12.0, 2H), 4.52 (dd, J=4.8, 8.4 Hz, 1H), 2.50-2.56 (m, 1H), 2.22-2.30 (m, 2H), 1.71-1.85 (m, 1H), 1.44-1.60 (m, 4H), 1.15-1.39 (m, 8H), 0.81-0.92 (m, 6H); 13C NMR (500 MHz, CDCl$_3$) 14, 14.6, 14.7, 23.1, 23.3, 23.6, 24.9, 25.8, 26.9, 29.4, 30.4, 31.1, 31.9, 32.3, 40.4, 71.6, 79.8, 121.7, 129.2, 129.4, 129.5, 129.8, 133.1, 152.7, 163.7, 167.3; ESI LRMS Calcd. for C20H28LiO4+[M+Li]: 339. Found: 338.

Example V

Screening Beta-Lactones for Activity Against Fatty Acid Synthase and Anti-Tumor Activity Compounds that have been synthesized using the invention synthesis method are tested for potency and selectivity in their ability to act as agonists of Fatty Acid Synthase (FAS) and its recombinant thioesterase domain. Based on the structure of Orlistat, it is determined that FAS makes two dominant contacts with the compound: one engaging the long beta-hydrophilic alkyl chain; and another that forms hydrogen bonds with the N-formyl leucine.

Enzyme Inhibition Studies.

A recombinant form of the thioesterase domain of fatty acid synthase was used in a substrate-based screen to measure the apparent K.sub.i of these greatly simplified Orlistat derivatives Importantly, Orlistat is an irreversible inhibitor of the FAS TE domain, as it forms an adduct with the active site serine. We presume that the beta-lactones discussed herein function via the same mechanism. Therefore, we report the results as apparent inhibition constants (app K.sub.i), as the term K.sub.i is usually used for reversible inhibitors.

4-Methylumbelliferyl heptanoate (4-MUH) was utilized as a substrate for FAS as it was found to provide the best signal to noise ratio and an acceptable turnover rate. The product of this substrate, 4-methylumbelliferone, fluoresces at 450 nM (excitation at 350 nM), providing a convenient readout of thioesterase activity. In this assay, the hydrolysis of 4-MUH is blocked by Orlistat, our lead antagonist with an apparent K.sub.i of 0.21. micro.M. The ability of the simple dialkyl-beta-lactones prepared by the ketene dimerization/hydrogenation process to act as antagonists against 4-MUH against recombinant FAS TE was measured by this assay (Table 5).

TABLE 5

| Antagonistic activity of beta-lactones toward recombinant FAS TE compared to Orlistat. | | |
|---|---|---|
| cmpd. | R | apparent $K_i$ (•micro•M) |
| | 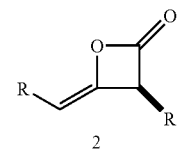 | |
| 2a | 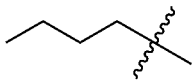 | 16.7 |

TABLE 5-continued

Antagonistic activity of beta-lactones toward recombinant FAS TE compared to Orlistat.

| cmpd. | R | apparent $K_i$ (•micro•M) |
|---|---|---|
| 2c | cyclohexyl-CH₂-CH(-)- | >100 |
| 2d | benzyl-CH(-)- | 5.04 ± 2.1 |
| 2f | MeO-(CH₂)₁₀-CH(-)- | 20.8 ± 1.4 |

Structure 2 (general): β-lactone with R-CH₂- at C4 and R at C3 (cis, wedge/dash)

| cmpd. | R | apparent $K_i$ (•micro•M) |
|---|---|---|
| trans-3a | n-pentyl | 4.01 ± 1.9 |
| trans-3b | cyclopentylmethyl | 6.7 ± 1.0 |
| trans-3c | cyclohexylmethyl | 6.3 ± 0.71 |
| trans-3d | benzyl | 3.3 ± 0.2 |
| trans-3f | MeO-(CH₂)₁₀- | — |

Structure 3 (general): β-lactone with R-CH₂- at C4 and R at C3 (trans)

| cmpd. | R | apparent $K_i$ (•micro•M) |
|---|---|---|
| Orlistat | | |
| 3a | n-pentyl | 23.1 ± 4.2 |
| 3b | cyclopentylmethyl | 13.5 ± 7.8 |
| 3c | cyclohexylmethyl | 7.7 ± 0.43 |
| 3d | benzyl | 2.5 ± 0.47 |
| 3e | H₃CO-C(=O)-CH₂- | >100 |
| 3f | MeO-(CH₂)₁₀- | 35.4 ± 5.3 |

Structure 8 (general): β-lactone with n-pentyl at C4 and both n-butyl and R at C3

| | | |
|---|---|---|
| 8a | CH₃ | 14.6 ± 4.0 |
| 8b | PhCH₂ | 19.2 ± 0.36 |
| 8c | CO₂Benzyl | 9.96 ± 2.8 |

Figure 13:
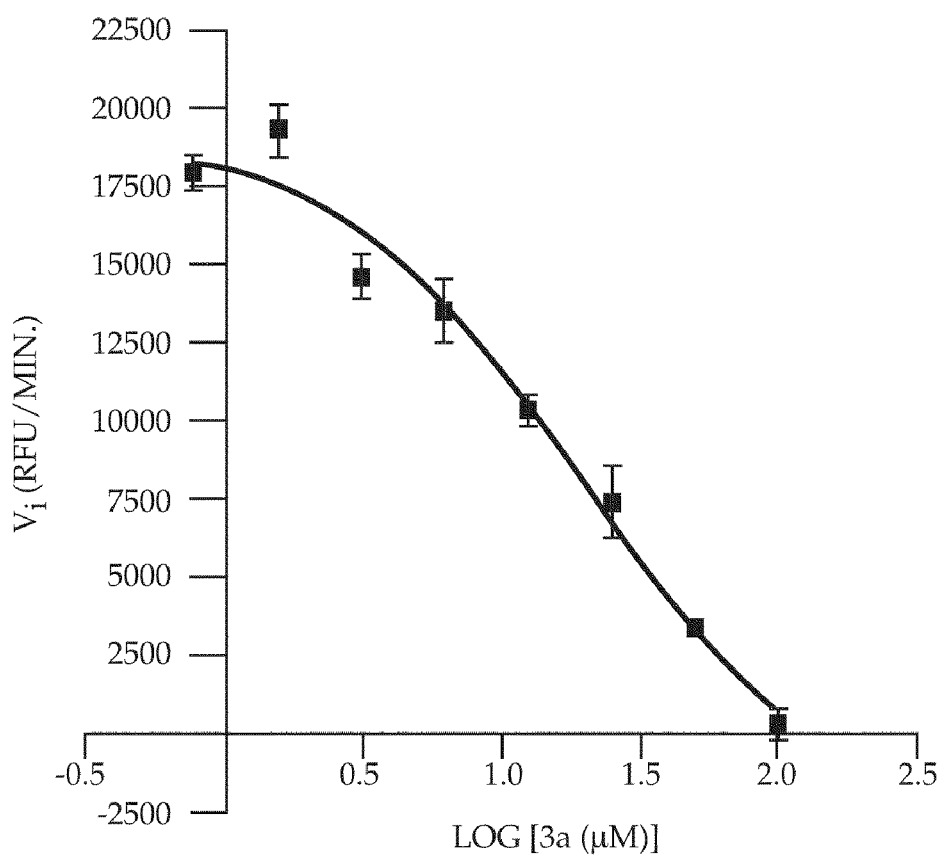
FIG. 13 is a dose-response curve from a fluorogenic assay illustrating the inhibition of FAS TE by beta-lactone 3a from Table 2, entry 1.

These simple dialkyl-beta-lactones are devoid of the aminoester side chain, which presumably serves as a recognition site and add some degree of water solubility. Nonetheless, the tested beta-lactones were able to inhibit FAS TE, and, in comparison to Orlistat, the potency of some of these compounds was only reduced by approximately 10-fold. (e.g., FIG. 13) Thus, these findings are very significant with respect to synthesizing active beta-lactone compounds using the current invention method.

Thus, there is herein described a scaleable methodology to prepare cis and trans-3,4-disubstituted-beta-lactones using a ketene dimerization/hydrogenation sequence from readily available acid chlorides in good overall yields and high enantioselectivity. This reaction could be run as a single-pot, two step process, but higher overall yields and optical purities were obtained upon isolation of the ketene dimer by silica gel chromatography and subsequent hydrogenation of the purified dimer at moderate pressures. Ketene dimers were found to be isolable and could be purified and their enantiomeric purity determined by chiral GC analysis. Enolization followed by alkylation and acylation of the cis-beta-lactones providing ready access to trisubstituted-beta-lactones in high diastereoselectivities. Trans-beta-lactones could be obtained by low temperature deprotonation and quenching. These highly simplified dialkyl-beta-lactones are analogous to Orlistat and were found to exhibit moderate inhibitory activity toward recombinant FAS TE as measured by enzymatic activity using recombinant protein and a fluorogenic assay. Further transformations of these optically pure ketene homodimers are being explored as a means to provide practical routes to beta-lactones more structurally analogous to Orlistat and expected to have higher affinity for FAS TE.

Methods

Fluorogenic Assay for Detection of Enzyme Inhibition.

Expression of the recombinant thioesterase domain of FAS was performed as described previously (Kridel, S. J.; Axelrod, F.; Rozenkrantz, N.; Smith, J. W. Cancer Res. 2004, 64, 2070 and Knowles, L. M.; Axelrod, F.; Browne, C. D.; Smith, J. W. J. Biol. Chem. 2004, 279, 30540) and large-scale expression was preformed by Invitrogen Corporation (Madison, Wis.). The synthetic fluorogenic substrate, 4-methylumbelliferyl heptanoate (4-MUH), was purchased from Sigma (St. Louis, Mo.). The reaction mixture consisted of 500 nM FAS TE in buffer A (100 mM Tris-HCl, 50 mM NaCl at pH 7.4) which was pre-incubated with 2.5. micro.L test beta-lactones dissolved in DMSO at concentrations of 0.32-100. micro.M at 37. deg.C. for 30 minutes. The reaction was initiated by addition of 5. micro.L of 1.25 mM 4-MUH in 1:1 DMSO:buffer A. The resulting fluorescence from liberated 4-methylumbelliferone was measured every five minutes at 350/450 nm for 40-60 minutes. Results are the average of triplicate time points. Each compound was tested at least twice, yielding essentially identical results.

Incorporation by Reference

Throughout this application, various publications, patents, and/or patent applications are referenced in order to more fully describe the state of the art to which this invention pertains. The disclosures of these publications, patents, and/or patent applications are herein incorporated by reference in their entireties, and for the subject matter for which they are specifically referenced in the same or a prior sentence, to the same extent as if each independent publication, patent, and/or patent application was specifically and individually indicated to be incorporated by reference.

Other Embodiments

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of the Formula VI:

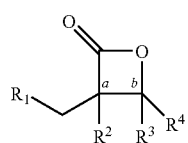

VI wherein $R_1$ is cyclopentyl, cyclohexyl, benzyl, $CO_2Me$ or MeO—$(CH_2)_9$—;

$R_2$, $R_3$ and $R_4$ comprises a hydrogen, an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group, or a combination thereof;

wherein $R_2$ is not phenyl or methyl when $R_1$ is benzyl or —$CO_2Me$; and wherein the stereochemistry at carbons a and b is R or S.

2. A compound of the Formula VI:

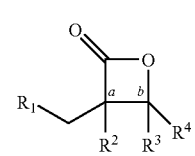

VI wherein $R_1$ and $R_4$ are n-butyl and $R_2$ and $R_3$ are hydrogen; and wherein the stereochemistry at carbons a and b is R or S.

3. A compound wherein the compound is a compound selected from the group consisting of (3R,4S)-3-butyl-4-pentyloxetan-2-one, (3R,4R)-3-butyl-4-pentyloxetan-2-one; (3R,4S)-3-butyl-3-methyl-4-pentyloxetan-2-one, (3S,4S)-3-benzyl-3-butyl-4-pentyloxetan-2-one; and (3S,4S)-benzyl 3-butyl-2-oxo-4-pentyloxetane-3-carboxylate.

4. A compound of the Formula VI:

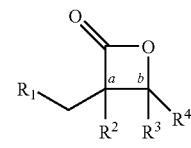

VI wherein $R_1$ is cyclopentyl, cyclohexyl, benzyl, $CO_2Me$ or MeO—$(CH_2)_9$—;

$R_2$, $R_3$ and $R_4$ comprises a hydrogen, an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group, or a combination thereof;

wherein $R_2$ is not phenyl or methyl when $R_1$ is benzyl or —$CO_2Me$;

wherein the stereochemistry at carbons a and b is R or S; and wherein said compound is synthesized using a method comprising the steps of:

(a) forming a ketene dimer from an acid chloride; and (b) hydrogenating the ketene dimer to generate a cis-beta-lactone.

5. A compound of the Formula VI:

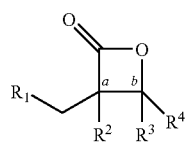

wherein $R_1$ is cyclopentyl, cyclohexyl, benzyl, $CO_2Me$ or MeO—$(CH_2)_9$—;

$R_2$, $R_3$ and $R_4$ comprises a hydrogen, an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group, or a combination thereof;

wherein $R_2$ is not phenyl or methyl when $R_1$ is benzyl or —$CO_2Me$;

wherein the stereochemistry at carbons a and b is R or S; and wherein said compound is synthesized using a method of comprising the steps of:

(a) forming a ketene dimer from an acid chloride;

(b) hydrogenating the ketene dimer to generate a cis-beta-lactone; and (c) performing an epimerization step further comprising the steps of:

(i) deprotonating the cis-beta lactone; and (ii) quenching the deprotonated species under low temperature.

6. A compound of the Formula VI:

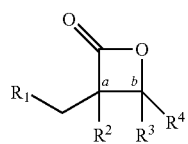

wherein $R_1$ is cyclopentyl, cyclohexyl, benzyl, $CO_2Me$ or MeO—$(CH_2)_9$—;

$R_2$, $R_3$ and $R_4$ comprises a hydrogen, an alkyl group, a cycloalkyl group, a heterocycloalkyl group, an alkoxy group, a hydroxyalkyl group, a halogenated alkyl group, an alkoxyalkyl group, an alkenyl group, an alkynyl group, an aryl group, a heteroaryl group, an aralkyl group, a hydroxy group, an amine group, an amide, an ester, a carbonate group, a carboxylic acid, an aldehyde, a keto group, an ether group, a halide, a urethane group, a silyl group, a sulfo-oxo group, or a combination thereof;

wherein $R_2$ is not phenyl or methyl when $R_1$ is benzyl or —$CO_2Me$;

wherein the stereochemistry at carbons a and b is R or S; and wherein said compound is synthesized using a method comprising the steps of:

(a) forming a ketene dimer from an acid chloride;

(b) hydrogenating the ketene dimer to generate a cis-beta-lactone; and (c) converting the cis-beta-lactone to a trisubstituted species.

7. The compound of claim 4, wherein the method is a one-pot synthesis method.

8. The compound of claim 4, wherein the ketene dimer formed in step (a) is isolated before the hydrogenation step.

9. The compound of claim 8, wherein the isolation of the ketene dimer is performed by silica gel purification.

10. The compound of claim 4, wherein the acid chloride has the formula VII below

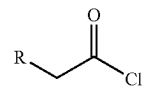

wherein R is cyclopentyl, cyclohexyl, benzyl, $CO_2Me$ or MeO—$(CH_2)_9$—.

11. The compound of claim 4 wherein the step of forming a ketene dimer from an acid chloride comprises using a catalyst wherein said catalyst is selected from the group consisting of QND, O-TBS QND, O-TMS QND, and O-TMS QUIN.

12. The compound of claim 11 wherein the catalyst is QND.

13. The compound of claim 11 wherein the catalyst is O-TMS QUIN.

14. The compound of claim 4 wherein the step of hydrogenating the ketene dimer comprises using a palladium on carbon catalyst.

15. The compound of claim 14 wherein the catalyst is at a concentration of about 1 mol % and 5 mol %.

16. The compound of claim 15 wherein the catalyst is at a concentration of about 1 mol %.

17. The compound of claim 14 wherein the catalyst is accompanied by an amine.

18. The compound of claim 17 wherein the amine is triethylamine.

19. The compound of claim 14 wherein the step of hydrogenating a ketene dimer is performed for 30 minutes at 30 psi $H_2$.

20. The compound of claim 4, wherein the method further comprises an epimerization step.

21. The compound of claim 20 wherein the epimerization step comprises the further steps of:

(a) deprotonating the cis-beta lactone; and (b) quenching the deprotonated species under low temperature.

22. The compound of claim 21 wherein the step of deprotonating is performed using lithium hexamethyldisilazide (LiHMDS) or related bases such as lithium diisopropylamide (LDA), sodium hexamethyldisilazide (NaHMDS), or lithium tetramethylpiperidide (LiTMP).

23. The compound of claim 21 wherein the step of quenching the deprotonated species is performed using acetic acid.

24. The compound of claim 4 further comprising converting the cis-beta-lactone to a trisubstituted species.

25. The compound of claim 24 wherein the converting step comprises alkylation or acylation.

26. The compound of claim 24 wherein the converting step comprises the further steps of:

(a) enolization of the cis-beta-lactone; and
(b) addition of electrophiles.

27. The compound of claim 26 wherein the enolization step is performed using LDA, LiHMDS or NaHMDS.

28. The compound of claim 26 wherein the electrophiles added to the enolated species from the group consisting of electrophiles.

29. The compound of claim 28 wherein the electrophile is a bulky electrophile or a smaller electrophile.

30. The compound of claim 26 wherein the electrophile comprises $CH_3$, benzyl or $CO_2Me$.

* * * * *